(12) United States Patent
Shultz et al.

(10) Patent No.: US 12,285,273 B2
(45) Date of Patent: Apr. 29, 2025

(54) MULTI-AXIAL JOINT LAXITY TESTING APPARATUS AND METHOD

(71) Applicant: University of North Carolina at Greensboro, Greensboro, NC (US)

(72) Inventors: Sandra Janine Shultz, Greensboro, NC (US); Randy Joe Schmitz, Oak Ridge, NC (US); James Avery Coppock, Durham, NC (US); Sam Seyedin, Greensboro, NC (US)

(73) Assignee: University of North Carolina at Greensboro, Greensboro, NC (US)

( * ) Notice: Subject to any disclaimer, the term of this patent is extended or adjusted under 35 U.S.C. 154(b) by 3 days.

(21) Appl. No.: 17/361,430

(22) Filed: Jun. 29, 2021

(65) Prior Publication Data

US 2022/0409142 A1 Dec. 29, 2022

(51) Int. Cl.
*A61B 5/00* (2006.01)
*A61B 5/11* (2006.01)

(52) U.S. Cl.
CPC ............ *A61B 5/702* (2013.01); *A61B 5/1121* (2013.01); *A61B 5/4585* (2013.01)

(58) Field of Classification Search
CPC .............................. A61B 5/702; A61B 5/4585
See application file for complete search history.

(56) References Cited

U.S. PATENT DOCUMENTS

| 5,645,079 A * | 7/1997 | Zahiri .................. A61F 5/3769 5/624 |
| 9,451,918 B2 | 9/2016 | Coelho Do Sameiro Espregueira Mendes |
| 2009/0124936 A1* | 5/2009 | Branch ............... A61B 5/4585 482/79 |
| 2011/0218461 A1* | 9/2011 | Cugat Bertomeu . A61B 5/1071 600/595 |

(Continued)

FOREIGN PATENT DOCUMENTS

| WO | 2014028288 A1 | 2/2014 |
| WO | 2020096955 A1 | 5/2020 |

OTHER PUBLICATIONS

"Pugh, L. et al., Current Concepts in Instrumented Knee-Laxity Testing; Oct. 21, 2008; The American Journal of Sports Medicine; vol. 37; pp. 199-200" (Year: 2008).*

(Continued)

*Primary Examiner* — Charles A Marmor, II
*Assistant Examiner* — Severo Antonio P Lopez
(74) *Attorney, Agent, or Firm* — NK Patent Law

(57) ABSTRACT

Knee joint laxity testing apparatus configured to measure knee laxity in three planes of motion includes a foot and ankle stabilization assembly including a foot plate, a heel clamp and a tibial clamp for securing a foot and an ankle of a person, an anterior-posterior (AP) loading assembly configured to apply an anterior/posterior loading on a knee of the person, and a thigh stabilization assembly including a proximal thigh fixation module and a distal thigh fixation (Continued)

module. The proximal thigh fixation module includes a thigh cradle and a pair of clamping arms for securing a thigh positioned on the thigh cradle. Each clamping arm is pivotable about a hinge. The distal thigh fixation module is operable to firmly hold a distal portion of a thigh of the person in place while a leg of the person is manipulated.

21 Claims, 19 Drawing Sheets

(56) References Cited

U.S. PATENT DOCUMENTS

| | | | | |
|---|---|---|---|---|
| 2012/0046540 | A1* | 2/2012 | Branch | A61B 5/459 600/407 |
| 2013/0204119 | A1* | 8/2013 | Coelho Do Sameiro Espregue Mendes | A61B 5/103 600/595 |
| 2017/0143250 | A1 | 5/2017 | Branch et al. | |
| 2017/0347942 | A1* | 12/2017 | Branch | A61B 5/4528 |
| 2017/0347945 | A1 | 12/2017 | Branch et al. | |
| 2017/0360512 | A1* | 12/2017 | Couture | A61B 34/30 |
| 2021/0251566 | A1 | 8/2021 | Shultz et al. | |

OTHER PUBLICATIONS

"Mines, D.; An Evaluation of Knee Joint Laxity, Mechanics and Muscle Activation Following Sustained Deep Flexion Kneeling; 2016; University of Waterloo; p. 30" (Year: 2016).*

"Collette, M, et al. Objective evaluation of anterior knee laxity; comparison of the KT-1000 and GNRB® arthrometers. Jan. 10, 2012. Knee Surgery, Sports Traumatology, Arthroscopy. vol. 20. p. 2234" (Year: 2012).*

"Genourob. Choose Your GNRB. Nov. 2, 2018. Genourob. pp. 1-3" (Year: 2018).*

ISA/KR; International Search Report and Written Opinion for International Patent Application No. PCT/US2019/059648 dated Apr. 8, 2020, 13 pages.

Shultz, Sandra J., et al., "Identifying Multiplanar Knee Laxity Profiles and Associated Physical Characteristics", Journal of Athletic Training, Apr. 30, 2012, vol. 47, Issue 2, 21 pages.

WIPO; International Preliminary Report on Patentability for International Patent Application No. PCT/US2019/059648 dated May 20, 2021, 10 pages.

ISA/US; International Search Report and Written Opinion for International Patent Application No. PCT/US2022/031984 dated Sep. 2, 2022, 10 pages.

WIPO: International Preliminary Report on Patentability for corresponding International Patent Application No. PCT/US2022/031984, dated Dec. 14, 2023, 8 pages.

* cited by examiner

MULTI-AXIAL JOINT LAXITY TESTING APPARATUS AND METHOD

TECHNICAL FIELD

The present disclosure relates to human joint testing, and particularly, to devices and methods for multi-axial joint laxity testing.

BACKGROUND

Prior devices for joint laxity measurement are expensive, take considerable training, take considerable time to gain accurate measurements, and still can lack reliability and agreement of measures between testers. Commercial laxity assessment devices (arthrometers) available in the market suffer from inconsistent and difficult measurements which has contributed to poor adoption of these devices by clinicians. Prior devices that do exist, only measure AP (anterior-posterior) laxity, or Internal-External rotation laxity. There is no specific device available for the purpose of measuring frontal plane knee laxity apart from X-ray examination. The need for knee laxity measuring equipment has increased in recent years, given two prospective studies that have independently determined that knee laxity is a strong predictor of ACL (anterior cruciate ligament) injury risk. Publications on knee laxity demonstrate clear sex-based differences in laxity, changes that can occur during the menstrual cycle and during exercise, and the biomechanical consequences of these changes. There are many clinical benefits to be had from the assessment of knee laxity, including injury risk screening, diagnosis of injury, and monitoring joint health/recovery over time post injury or surgery.

There is accordingly a need for a device that is easily accessible and can be efficiently used by clinicians and other end users for mass screening purposes that can accurately identify those with increased laxity and screen for those at risk, as well as for the purposes of injury diagnosis and rehabilitation.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

Disclosed herein is a knee joint laxity testing apparatus. In various embodiments, the apparatus comprises a foot and ankle stabilization assembly including a foot plate, a heel clamp, and a tibial clamp for securing a foot and an ankle of a person, an anterior-posterior (AP) loading assembly configured to apply an anterior/posterior loading on a knee of the person, and a thigh stabilization assembly including a proximal thigh fixation module and a distal thigh fixation module, the proximal thigh fixation module comprising a thigh cradle and a pair of clamping arms for securing a thigh positioned on the thigh cradle, each clamping arm pivotable about a hinge, the distal thigh fixation module operable to firmly hold a distal portion of a thigh of the person in place while a leg of the person is manipulated. The apparatus is configured to measure knee laxity in three planes of motion. According to one embodiment, According to one embodiment, the three planes of motion comprise anterior-posterior translations; varus-valgus rotations; and internal-external rotations.

According to one embodiment, a spacing between bases of the clamping arms is adjustable.

According to one embodiment, the foot and ankle stabilization assembly contacts a lower tibia, a heel, and a forefoot of the person.

According to one embodiment, the heel clamp is movable about an x-axis and about a y-axis for fixedly positioning the heel clamp at a plurality of points on a plane.

According to one embodiment, each of the heel clamp and the tibial clamp is adjustable independent of the other.

According to one embodiment, the anterior-posterior (AP) loading assembly provides anterior/posterior loading solely in a sagittal plane.

According to one embodiment, the anterior-posterior (AP) loading assembly further comprises a strap configured to surround an upper leg of the person.

According to one embodiment, the anterior-posterior (AP) loading assembly further comprises a handle, and a force transducer in line with the handle.

According to one embodiment, the handle is one of: slidable along two linear bars and includes a position sensor.

According to one embodiment, the anterior-posterior (AP) loading assembly further comprises a horizontal bar spanning a space between the two linear bars.

According to one embodiment, the distal thigh fixation module is positioned between the anterior-posterior (AP) loading assembly and the thigh cradle.

According to one embodiment, the distal thigh fixation module comprises two condylar clamps and a patella pad affixed to a horizontal bar spanning a space between two linear bars attached to the thigh cradle, wherein the horizontal bar is configured to swing about a linear bar to facilitate removal of a leg of the person from the apparatus.

According to one embodiment, the foot and ankle stabilization assembly further comprises an Internal-External (IE) rotational fixture mounted on a carriage.

According to one embodiment, the carriage is attached to a linear track or a curvilinear track to facilitate varus-vargus laxity testing.

According to one embodiment, the foot and ankle stabilization assembly further comprises rotational mechanisms to allow for Internal-External (IE) rotation and varus-valgus (VV) rotation.

According to one embodiment, the foot and ankle stabilization assembly is adjustable in length and width to accommodate and secure different size feet.

Disclosed herein is a system for knee joint laxity testing. In various embodiments, the system comprises a knee joint laxity testing apparatus engageable with a person's knee, the knee joint laxity testing apparatus comprising a thigh stabilization assembly, a foot and ankle stabilization assembly, and an anterior-posterior (AP) loading assembly. The thigh stabilization assembly includes a proximal thigh fixation module and a distal thigh fixation module. The proximal thigh fixation module comprises a thigh cradle and a pair of clamping arms for securing a thigh positioned on the thigh cradle. Each clamping arm is pivotable about a hinge. The distal thigh fixation module is operable to firmly hold a distal portion of a thigh of the person in place while a leg of the person is manipulated. The foot and ankle stabilization assembly includes a foot plate, a heel clamp, and a tibial clamp for securing a foot and an ankle of a person. The anterior-posterior (AP) loading assembly configured to apply an anterior/posterior loading on a knee of the person. The knee joint laxity testing apparatus configured to measure knee laxity values in three planes of motion. A controller coupled to the knee joint laxity testing apparatus is configured to receive the measured knee laxity values in three planes of motion. The controller further configured to display, on a user interface of a computing device, the measured knee laxity values in three planes of motion.

According to one embodiment, the computing device comprises a processor communicably coupled to at least one memory; and program instructions which when executed by the processor cause the processor to: receive, from the controller, the measured knee laxity values in three planes of motion, and display, on the user interface of the computing device, a level of deviation of a measured knee laxity value from a predetermined value.

According to one embodiment, the controller is in communication with at least one motor configured to perform one of: anterior-posterior translations; varus-valgus rotations; and internal-external rotations.

According to one embodiment, the controller is in communication with at least one sensor configured to sense one or more of a force and a displacement resulting from one of: anterior-posterior translations; varus-valgus rotations; and internal-external rotations.

Disclosed herein is a method for measure knee laxity with a knee joint laxity testing apparatus. In various embodiments, the method comprises measuring knee laxity values in three planes of motion with a knee joint laxity testing apparatus engageable with a person's knee. The knee joint laxity testing apparatus comprises a thigh stabilization assembly, a foot and ankle stabilization assembly, and an anterior-posterior (AP) loading assembly. The thigh stabilization assembly includes a proximal thigh fixation module and a distal thigh fixation module. The proximal thigh fixation module comprises a thigh cradle and a pair of clamping arms for securing a thigh positioned on the thigh cradle. Each clamping arm is pivotable about a hinge. The distal thigh fixation module is operable to firmly hold a distal portion of a thigh of the person in place while a leg of the person is manipulated. The foot and ankle stabilization assembly includes a foot plate, a heel clamp, and a tibial clamp for securing a foot and an ankle of a person. The anterior-posterior (AP) loading assembly is configured to apply an anterior/posterior loading on a knee of the person.

According to one embodiment, the method further comprises receiving, by a controller coupled to the knee joint laxity testing apparatus, the measured knee laxity values, and, displaying, on a user interface of a computing device, the measured knee laxity values.

DETAILED DESCRIPTION

Figure 1:
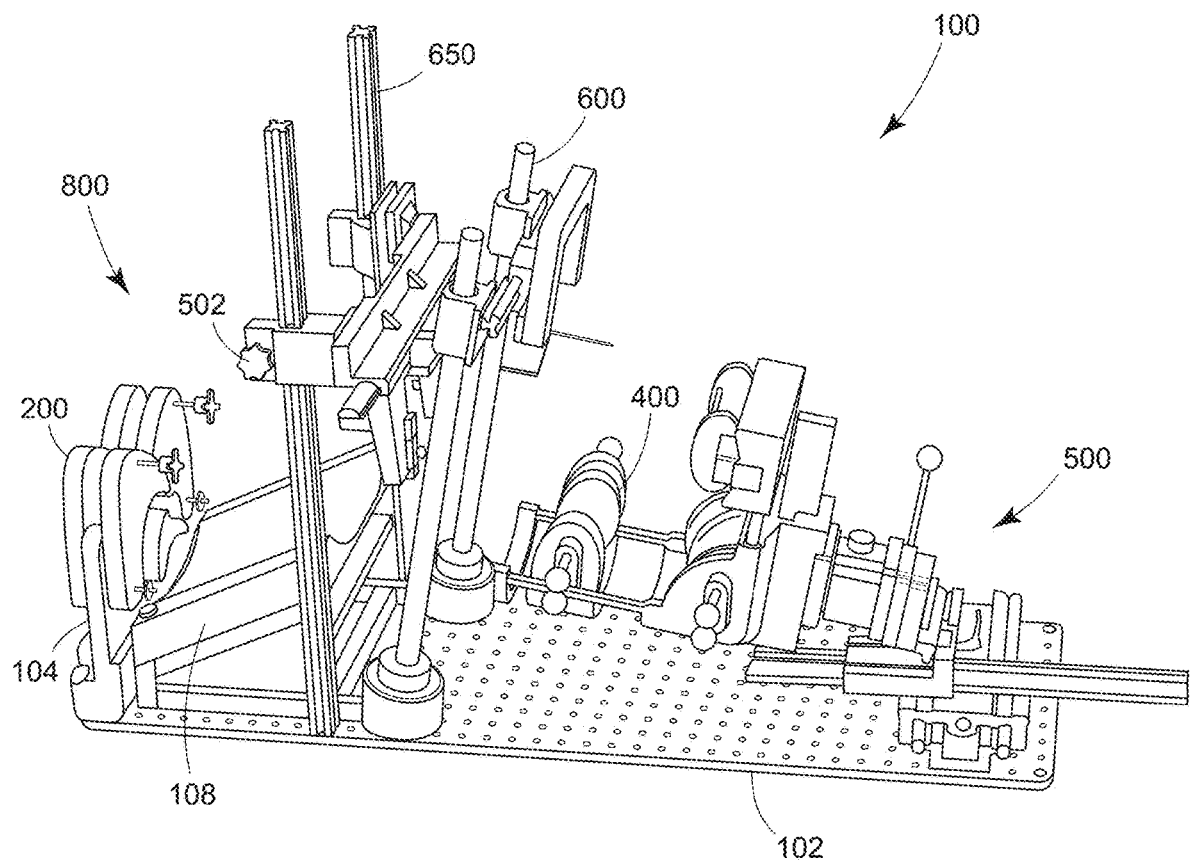
FIG. 1 is a side perspective view of a multi-axial joint laxity testing apparatus, according to at least one embodiment.

The following description and drawings are illustrative and are not to be construed as limiting. Numerous specific details are described to provide a thorough understanding of the disclosure. However, in certain instances, well-known or conventional details are not described in order to avoid obscuring the description. Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification. For example, some embodiments can be partially or fully automated whereas other embodiments may be set up for 100% manual operations.

Like reference numbers used throughout the drawings depict like or similar elements. Unless described or implied as exclusive alternatives, features throughout the drawings and descriptions should be taken as cumulative, such that features expressly associated with some particular embodiments can be combined with other embodiments.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

As used herein, the term "end user" includes healthcare professionals and researchers who assess knee joint health, treat, and rehabilitate knee injuries that include but are not limited to, physicians, physical therapists, orthopedic specialists, orthotists and athletic trainers.

According to various embodiments of the presently disclosed subject matter, a novel instrumented knee ligament/laxity testing apparatus as disclosed herein provides for conducting laxity tests to obtain objective measures of knee joint rotational displacement in the frontal (VV, varus-valgus laxity) plane, transverse (IE, internal-external rotation knee laxity) plane, and translational displacement in the sagittal (AP, anterior-posterior knee laxity) plane. Laxity is operationally defined as the translational or rotational displacement of the tibia/fibula relative to the femur under an applied load. AP laxity tests the isolated integrity of the anterior (ACL) and posterior (PCL) cruciate ligaments. VV laxity tests the isolated integrity of the medial and lateral collateral ligaments. IE laxity tests the integrity of both cruciate and collateral ligaments.

In various embodiments, the subject matter as disclosed herein advantageously provides for the ability to quickly, accurately and reliably perform objective assessments of knee laxity in three planes of motion. Embodiments as disclosed herein can advantageously amplify and augment the subjective abilities of end users. In some embodiments, the novel instrumented knee ligament/laxity testing apparatus as described herein is automated and can include a system such as system 700 (see FIG. 18) comprising hardware, software and an automated patient interface for conducting the laxity tests as described herein. Embodiments as disclosed herein can accordingly allow for automated knee assessment methods that could address the limitations of commercially available devices. In at least one embodiment, a robotic medical device is provided that is configured to emulating assessments of knee joint laxity that is otherwise subjectively made by end users having substantial training in the field, for example. Accordingly, while some embodiments can be partially or fully automated, other embodiments may be set up for 100% manual operations.

Laxity is an important measurement because it assists in the diagnosis of ligament injury and joint integrity. Laxity is defined as "the amount a joint deviates from its initial position when a force is applied to it." The deviation is largely restrained by the stabilizing ligaments. Laxity assessments inform an end user such as, for example, a clinician regarding an intervention plan that can avoid injury or that can support a patient's recovery from injury. In practice, end users including healthcare professionals use their hands to move a patient's knee joint for a subjective assessment of laxity, thus assessing ligament integrity. During testing for ligament integrity, end users such as clinicians are most commonly subjectively assessing displacement of the joint during passive motion (excursion), and the degree of tissue resistance at the end of the joint range of motion (end feel). Common assessments made by hand in practice often fail to provide a reliably objective metric of knee laxity. By contrast, the measurements made by the embodiments as disclosed herein are designed to emulate some of the hand-made assessments but in a more automated, objective and reproducible fashion. The embodiments as disclosed herein are designed to advantageously conduct three tests to assess laxity in three plans of motion: the anterior-posterior laxity, the varus-valgus rotational laxity and the interior-exterior rotational laxity.

Anterior-posterior knee laxity (APKL) test measures the displacement of the knee joint as force is applied from the posterior side of the joint toward the anterior side of the joint (and visa-versa) when angle between the thigh and the tibia/fibula is fixed at an angle of approximately 25-30 degrees. During this test, both the force applied to the knee joint, and the resulting displacement of the knee joint are measured, displayed and recorded. The loci of the force-displacement curves provide diagnostic information, including the "end feel" as the resistance to force applied increases, reducing movement and forming a "plateau" of displacement. Embodiments as disclosed herein can take measurements somewhat similar to a manual Lachman assessment.

Varus-valgus rotational laxity (VVRL) relates to valgus deflection and varus deflection. Valgus deflection first occurs as force is applied against the interior (medial) side of the shank or tibia/fibula causing the distal segment of the joint to pivot more laterally. Conversely, varus deflection occurs as force is applied to the exterior (lateral) side of the shank or tibia/fibula, resulting in medial deflection of the distal segment of the knee joint. As in anterior-posterior testing, this test is done while the thigh and shank are fixed at an angle of from 0-30 degrees. During this test, both the force applied to the knee joint, and the resulting displacement of the knee joint are measured, displayed and recorded. The loci of the force-displacement curves provide diagnostic information, including the "end feel" as the resistance to force applied increases, reducing movement and forming a "plateau" of displacement. Embodiments as disclosed herein can take measurements somewhat similar to the manual valgus-varus stress test.

Interior-exterior rotational laxity (IERL) test corresponds to the displacement of the knee joint as the tibia/fibula is rotated along its long axis (through the tibia/fibula) first toward the exterior (lateral) side of the joint and then to the interior (medial) side of the joint when angle between the thigh and the tibia/fibula is fixed at an angle from 0-30 degrees. Embodiments as disclosed herein can take measurements somewhat similar to a simple tibia/fibula rotation manual assessment.

As used herein, the term "clinical data registry" is a clinical data registry records information about the health status of patients and the health care they receive over varying periods of time. Clinical data registries typically focus on patients who share a common reason for needing health care. As used herein, the term "end feel" relates to the tactile feedback sensed by the clinician when force is applied by hand to displace the knee joint. As the joint displacement reaches its full range, resistance to displacement rapidly occurs and creates end feel.

A multi-axial joint laxity testing apparatus 100 (may be alternately referred to herein as "apparatus 100" or "apparatus" or "device") according to at least one embodiment is shown in FIG. 1. Apparatus 100 can operate as a portable (tabletop) knee arthrometer for accurate measurement of multi-planar knee joint laxity with minimal time and training required for the technician performing the testing on a subject/patient. Knee joint laxity characterizes the integrity of the cruciate and collateral ligament structures, which play a critical role in maintaining a healthy, stable knee during activities of daily living and sport. Laxity is operationally defined as the translational or rotational displacement of the tibia/fibula relative to the femur under an applied load. Instrumented assessment of knee joint laxity using apparatus 100 can have many clinical applications. For example, apparatus 100 can be used to screen for knee injury risk potential, to diagnose ligament injuries (in conjunction with clinician and MRI evaluations), to provide evidence of successful repair and healing of surgical repaired of reconstructed ligaments post-surgery and rehabilitation, and to measure progression of joint diseases such as osteoarthritis, and to serve as a prescription for custom knee bracing, among others. With these and related purposes in mind the apparatus 100 is designed with the many novel and advantageous features. Apparatus 100 can advantageously be used for accurately measuring knee laxity in 3 planes of motion in 5 minutes or less with minimal training.

Apparatus 100 can improve limb stabilization to reduce skin movement artifact associated with soft tissue deformation. Both data from the literature and clinician feedback speak to concerns about inadequate limb stabilization (e.g., stabilization of the thigh, positioning of the lower leg) whereby control of tissue movement artifact is reduced, which contributes to both random and systematic error during laxity test. Apparatus 100 is designed with a thigh stabilization system that can securely fix the thigh during apparatus manipulation of the tibia/fibula in all planes of motion. Apparatus 100 further includes a movable shank system that can be customize to each patient's leg to position the tibia/fibula relative to the femur in a reproducible and standardized manner for accurate comparison within and between patients and within and between testers. These stabilization mechanisms are intended to increase measurement precision and reproducibility. Apparatus 100 can be used to measure bone movement as validated against direct imaging.

Embodiments described herein advantageously provide for improved accurate measurement of laxity (displacement of the tibia/fibula relative to the femur) that represents true joint motion and improved diagnostic accuracy. The embodiments advantageously operate to prevent or limit undesirable thigh motion during laxity testing by firmly stabilizing the thigh while simultaneously providing for manipulating the lower leg during laxity testing. Existing devices are typically not capable of fully stabilizing the thigh, and as a result these devices have come under criticism for their measurement validity and reliability. By contrast, the embodiments described herein advantageously provides for superior stabilization, measurement accuracy and precision. The embodiments provide numerous improvements over International Patent Application No. WO 2020/096955 A1, the contents of which are incorporated herein by reference in its entirety. Apparatus 100 provides for minimizing or eliminating movement artifact and thereby prevent overestimation of internal-external and varus-valgus laxity.

According to various embodiments, apparatus 100 includes a thigh stabilization element in the form of thigh stabilization assembly 800, and a lower leg and foot and ankle stabilization element in the form of foot and ankle stabilization assembly 400 that are both attached to a same base that can allow isolation of laxity testing in each plane of motion (while locked in the other two planes of motion) with a single positioning of the subject/patient. Thigh stabilization assembly 800 includes a proximal thigh fixation module 200 and a distal thigh fixation module 650. To use apparatus 100, an individual can be positioned in the device atop a treatment table, lying supine with the lower extremity positioned in the thigh cradle (stabilized segment), the lower leg and foot positioned in the leg cradle (moveable segment) such that the knee joint is positioned in the desired amount of tibial rotation and knee flexion; alternately the individual can be seated in a special purpose chair that is configured for use with apparatus 100.

Figure 11A:
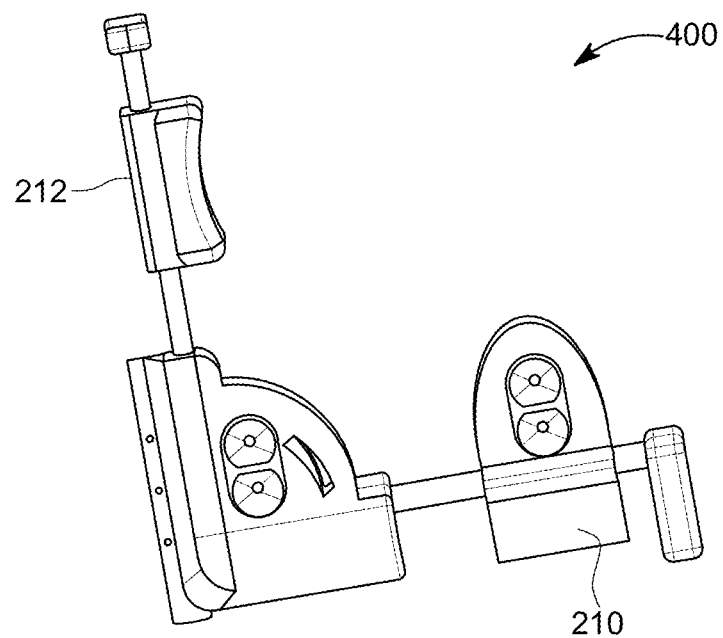
FIG. 11A is a side perspective view of a foot and ankle stabilization assembly forming part of a multi-axial joint laxity testing apparatus, according to at least one embodiment.
Figure 11B:
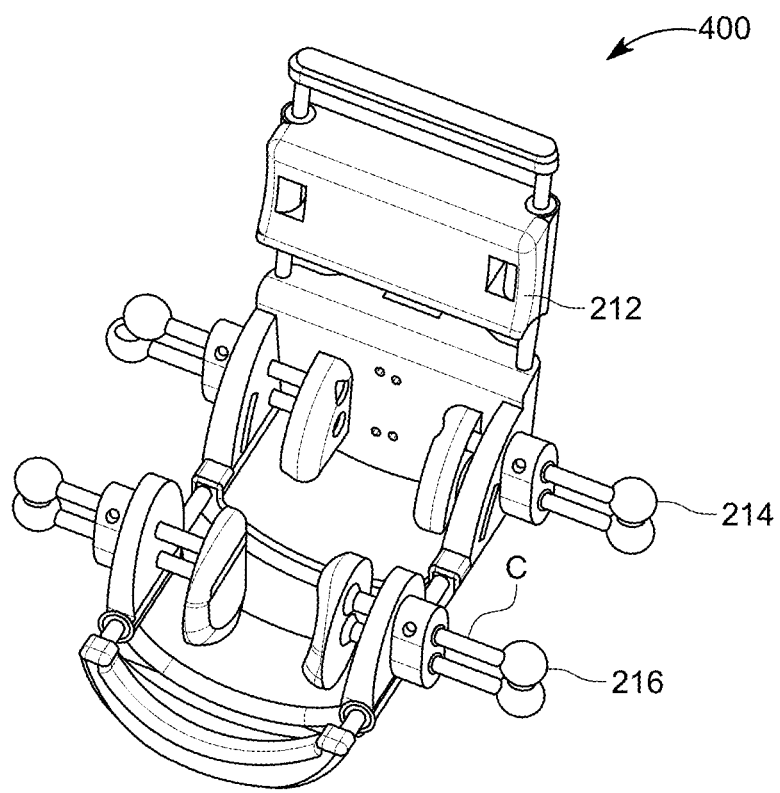
FIG. 11B is a front perspective view of a foot and ankle stabilization assembly forming part of a multi-axial joint laxity testing apparatus, according to at least one embodiment.
Figure 12:
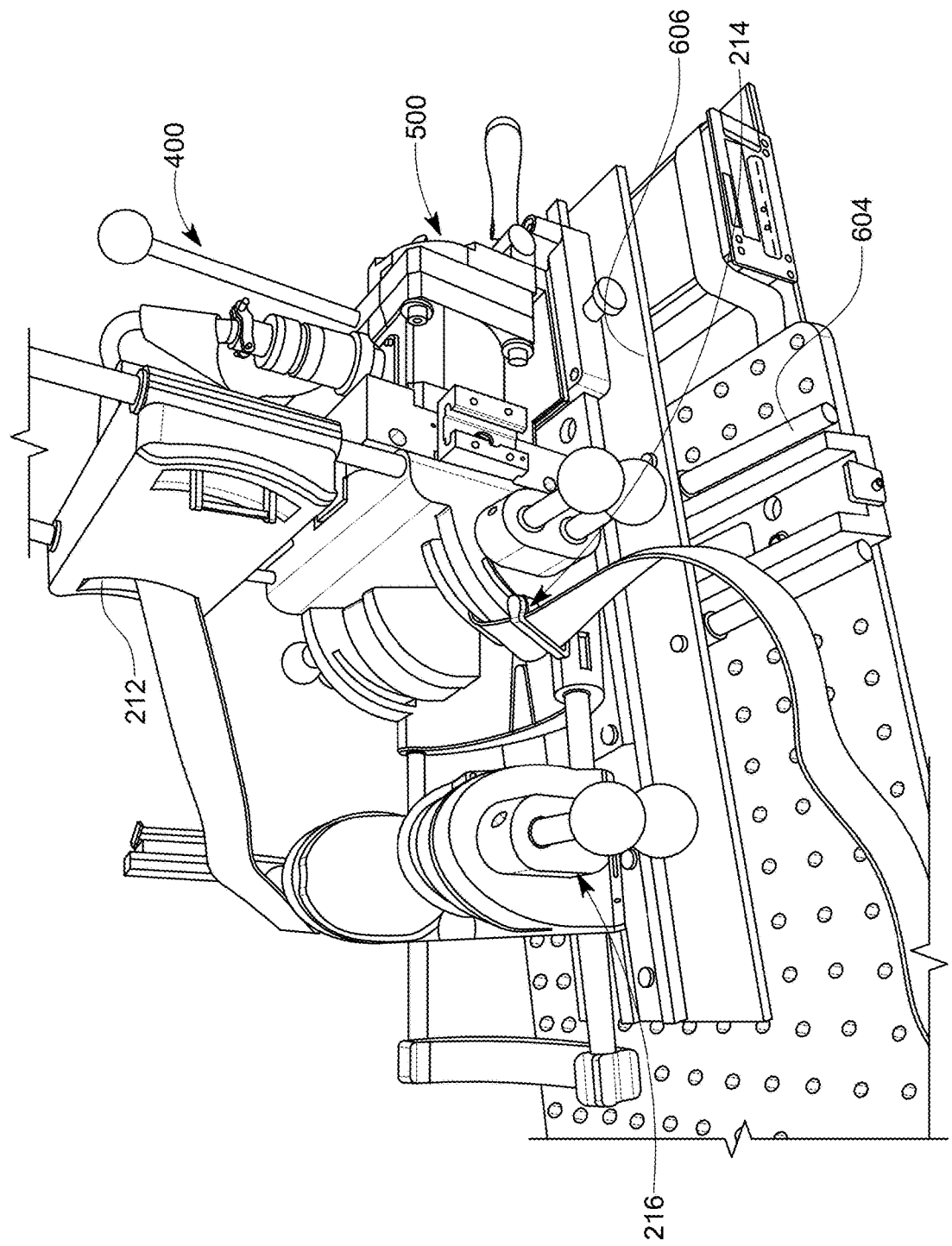
FIG. 12 is a side perspective view of a foot and ankle stabilization assembly secured to a based and forming part of a multi-axial joint laxity testing apparatus, according to at least one embodiment.

Foot and ankle stabilization assembly 400 (see, for example, FIG. 11A and FIG. 11B) forming part of apparatus 100 includes a 3-point clamping setup provided at the lower tibia/fibula (tibial clamp 216), the heel (heel clamp 214) and the forefoot (foot plate 212), to allow the lower leg and foot move as one rigid segment. Foot and ankle stabilization assembly 400 includes foot plate 212, heel clamp 214, tibial clamp 216 and posterior leg support 210. Tibial clamp 216 and heel clamp 214 can be independently adjusted to accommodate any width of foot, heel or leg. Heel clamp 214 at the lower leg includes a circular bearing that allows each side of heel clamp 214 to effectively conform to the contour of the lower leg, and this provides both comfort and superior stabilization. The clamp at the foot can be adjusted up and down as well as side to side to adjust to length and width of foot so that the position of the clamp interfaces with the foot at the metatarsal heads. The heel clamp is accordingly movable about an x-axis and about a y-axis for fixedly positioning the heel clamp at a plurality of points on a plane.

Figure 2:
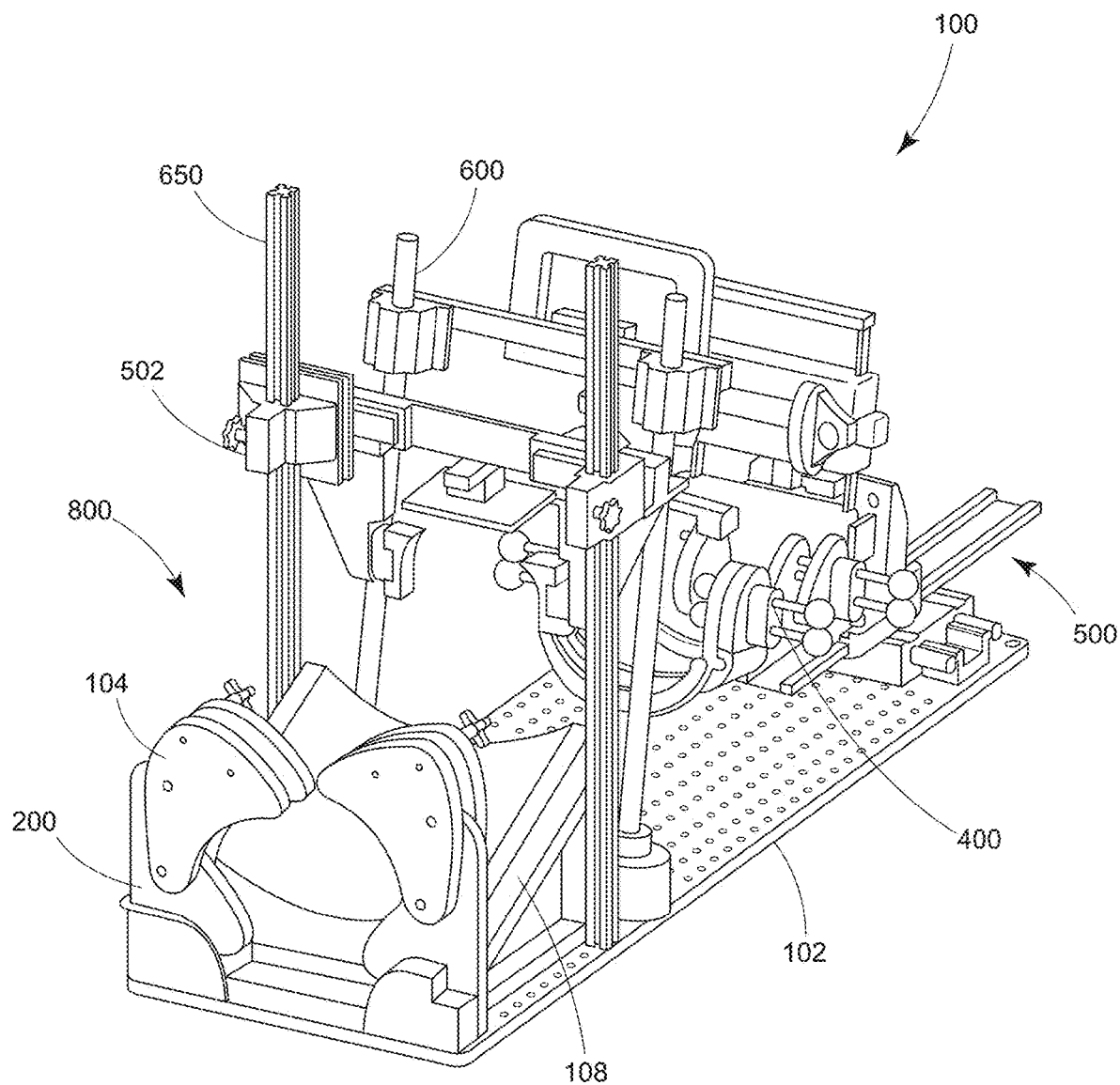
FIG. 2 is a front perspective view of a multi-axial joint laxity testing apparatus, according to at least one embodiment.

Foot and ankle stabilization assembly 400 is attached at its base to the heel mechanism and linear track that is used to properly position the leg during AP testing, and manipulate the leg during VV and IER testing (see FIG. 2). The foot and ankle stabilization system consists of a rigid posterior leg and foot plate and a series of clamps that is designed to rigidly stabilize the foot such that the lower leg move as one unit during internal-external rotation laxity testing. Within foot and ankle stabilization assembly 400 (see FIG. 11A and FIG. 11B), foot plate 212 allows the forefoot support to be adjusted to the patient's foot size (see FIG. 11A). The leg is secured above the ankle with a ratcheting type "anklet" that extends from the posterior leg and foot plate and can be positioned at the right distance from the ankle joint (see FIG. 11B) and adjusted in width and contour to accommodate different tibia/fibula sizes and shapes. Thus, the anklet clamps can move up and down, toward one another, and individually pivot both medial-laterally and inferior-superior to firmly stabilize tibial clamp 216. The foot is secured by clamping the heel on either side and the metatarsal heads (forefoot) on either side that extend from the posterior leg and foot plate. Each of heel clamp 214 and tibial clamp 216 can be independently adjusted and then held firmly in place by a ratcheting type of slide or screw adjustment. An optional strap across the anterior ankle and toes may be used to secure the foot within the foot plate. Firm cushioning may be provided on the surface of each clamp to assist in holding the foot and leg securely, and for comfort.

As measured using system 700 as disclosed herein, anterior-posterior displacement measures the movement of the patient's knee in the sagittal plane (somewhat like the Lachman test). With the thigh fixed, the anterior-posterior movement of the tibia/fibula relative to the femur is measured as force increases from zero to 150 N. As measured using system 700, lateral (varus-valgus) displacement measures the movement of the patient's knee in the Frontal plane (somewhat like the valgus-varus stress tests). With the thigh securely fixed, the tibia/fibula is moved under a medial-lateral directed rotational force about the knee joint, from zero to 10 Nm. As measured using system 700, internal-external rotational displacement measures the movement of the patient's knee in the transverse plane. With the thigh securely fixed, the tibia/fibula is rotated about its long axis under internal-external rotational force of zero to 5 Nm. In at least one embodiment, a load cell secured at the point at which the force is applied can be configured to record a torque applied based on known force and moment arm distance from the joint. The system can be fully automated so that it can cycle through each plane of motion (or isolated motions as desired), without requiring the hands of the end user or clinician (alternately referred to herein as the "tester"), whereby a tester dependent error can inadvertently be introduced. In a further embodiment, in order to reduce the cost of the system and to simplify the size and scope of the system, a manual version is provided whereby the components of the system and/or the knee of the patient/subject can be pushed/pulled along linear tracks to ensure a true planar motion in each direction, thus greatly reducing tester error.

According to various embodiments, conditioning trials at lower (and incrementally increasing loads) can include 3 to 5 test trials. To improve accuracy, it is important that the testing limb be firmly fixed in the device such that movement of the device accurately represents movement of the bones (tibia/fibula and femur). Accordingly, in various embodiments, proximal thigh fixation module 200, distal thigh fixation module 650, and ankle stabilization assembly 400 can be designed to tightly "form fit" around the contours of the limb. Accordingly, the system as described herein can include thigh stabilization assembly 800 (that includes a proximal thigh fixation module and a distal thigh fixation module) along with an ankle stabilization assembly that operate in conjunction with each other to ensure that the thigh cradle form fits around the contours of the limb and is held stable while the leg is manipulated. Precision sensors placed on the apparatus as well as on the limb can operate to cancel out any movement artifact whereby the system and/or apparatus can accurately measure laxity in all three planes of motion. The system and/or apparatus can accordingly allow for a quick and easy measurement of tri-planar knee laxity. The system and/or apparatus can also eliminate the need for an experienced end user or clinician to provide positioning instruction, thus removing as much tester error as possible. The system and/or apparatus can furthermore provide for objective measures validated against true bony motion which is the gold standard (e.g., x-ray, cadaver testing with bone pins) that can be documented.

Figure 19:
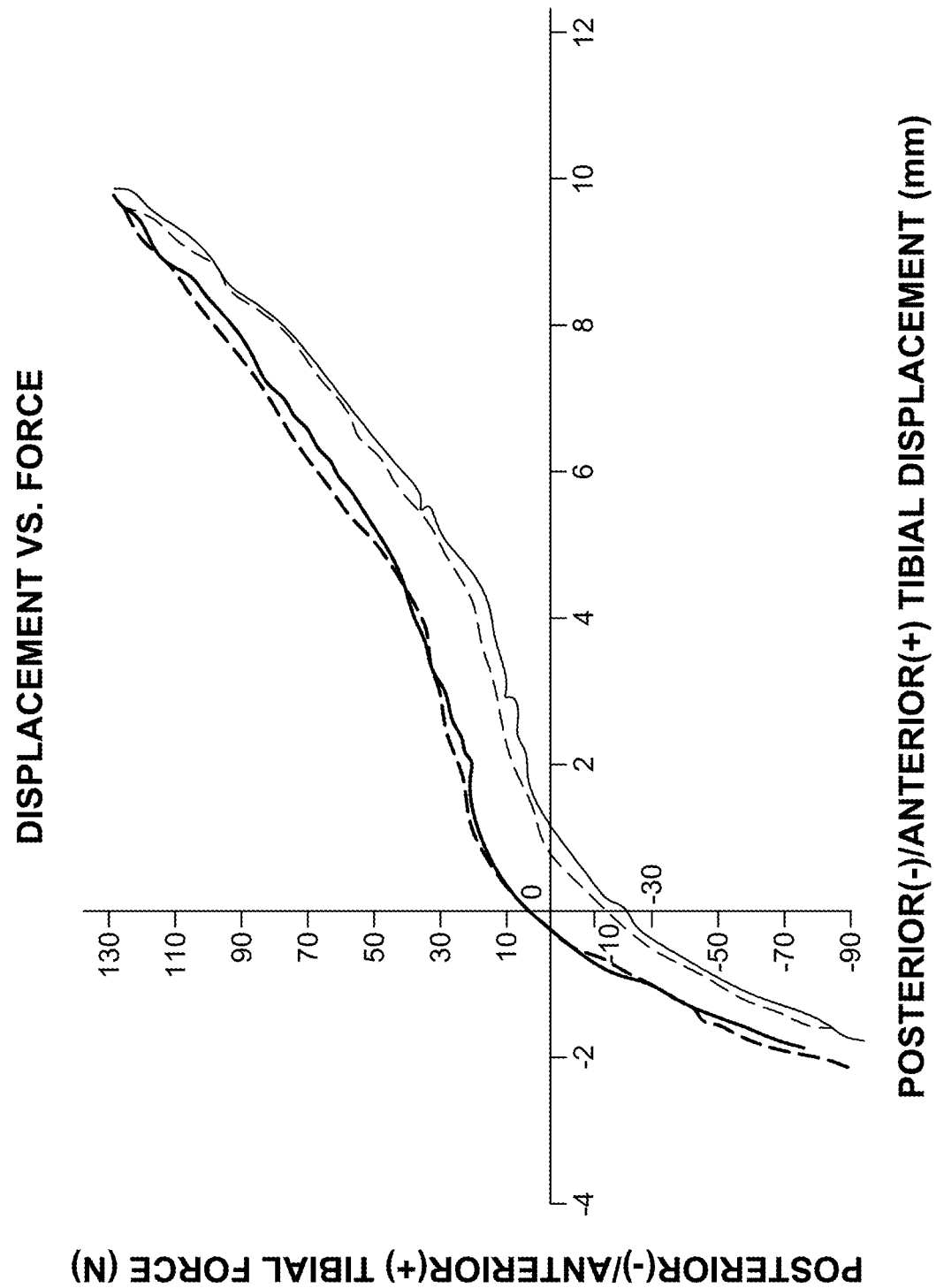
FIG. 19 is a graphical representation of a feedback display illustrating relationship between mechanical displacement and the force applied as measured by multi-axial joint laxity testing apparatus, according to at least one embodiment.

The system 700 and/or apparatus 100 can include software configured to measure displacement at a fixed load and constructing a load-displacement curve (for example, as shown in FIG. 19) to quantify joint stiffness/compliance using accompanying software. The software would also calculate relaxation curves, and would allow input of subject height, weight and femur and tibia/fibula length so that laxity values can be normalized to body size (this is not a feature of current systems). Thigh cradle 108, the foot and ankle stabilization assembly and/or the heel and linear slide can be equipped with a sliding caliper to accurately and efficiency record femur and tibia/fibula segment lengths.

Apparatus 100 is fully automated in some embodiments such that it can mechanically load the limb in a reproducible manner, removing human tester error. However, in some embodiments, apparatus 100 may be partially automated while in other embodiments, apparatus 100 may be fully manual. Tester error accounts for a substantial portion of the total measurement error of current devices. Multiple sources of measurement inconsistency resulting from tester error include hand size and dominance, examiner strength, and the control of rate, direction and magnitude of the applied load. As such, the level of examiner training has a substantial effect on precision and reproducibility of measures. In one embodiment, apparatus 100 does not include automation, i.e., apparatus 100 can be a manual version. Whether apparatus 100 is manual or fully automated, motion in each plane will be guided by a track system, which ensures consistent and repeatable motion in each plane. The manual version can reduce tester error by improved stabilization and positioning of the patient, and by controlling the direction and magnitude of the applied load, thereby rendering the apparatus clinician friendly while simultaneously reducing the level of examiner/tester training that is required. A fully automated apparatus 100 can further remove this source of measurement variation by standardizing the rate of the loading, making the apparatus clinician friendly and accurate in the hands of clinicians of various experience and training. Advantageously, in using the apparatus 100, the patient is stabilized (thigh and foot) as measurements are acquired. It is to be noted that the linear, rotational or curvilinear track system(s) upon which each motion occurs can ensure that the same motion is consistently achieved in each trial and patient.

In the embodiment of apparatus 100 illustrated in FIG. 1, the elevated components such as thigh stabilization assembly 800, an AP loading assembly 600, a foot and ankle stabilization assembly 400 and heel and linear slide 500 are, in some form, attached to base 102. This ensures that all components lie on a consistent and definite coordinate system, allowing end users to firmly secure the patient's limb and accurately calculate force and displacement outputs. Base 102, in the illustrated embodiment, provides a contiguous platform that is easily portable to and from a tabletop. This design can ensure that measurements can be made based on known distances, reducing measurement error and increasing measurement reliability. Above the base 102, apparatus 100 thus includes a thigh stabilization assembly 800, an AP loading assembly 600, a foot and ankle stabilization assembly 400 and heel and linear slide 500. This set up prevents unintended rotation of the tibia/fibula during AP translation. This set up further allows for providing a manual version in addition to an automated version. During manual load application, the apparatus is configured to ensure that: (1) the AP motion would occur solely in the sagittal plane, and (2) the motion is applied uniformly irrespective of who the clinician conducting the test might be. Apparatus 100 may further include a strap around the upper tibia and fibula. Apparatus 100 further includes a force transducer in line with a handle 605, which is moved along two linear bars to ensure that the force is uniformly applied through the tibia/fibula. This can provide for ease in applying force as compared to other manual predicate devices.

Distal thigh fixation module 650 includes U-bar assembly 502 that supports patella pad 142 and condyle clamps 144. Distal thigh fixation module 650 further includes vertical height adjustment bars 304 positioned at the distal end of the thigh cradle, with vertical height adjustment bars 304 forming part of U-bar assembly 502. In various embodiments, patella pad 142 and condyle clamps 144 may be mounted to a horizontal bar that is adjustable in height along two vertical height adjustment bars 304 that arise from the distal thigh cradle to firmly stabilize the distal thigh. Distal thigh fixation module 650 is designed for optimal fixation of the thigh in the device, and is applicable for all 3 laxity tests, not just AP loading. U-bar assembly 502 allows for improved clinician and patient interface with the device, and ease of operation. U-bar assembly 502 may include a patella pad and a swing arm to allow the horizontal bar to swing out of the way when the patient is positioned in the device. This provides for improved patient comfort, particularly those with an injured knee.

Figure 4:
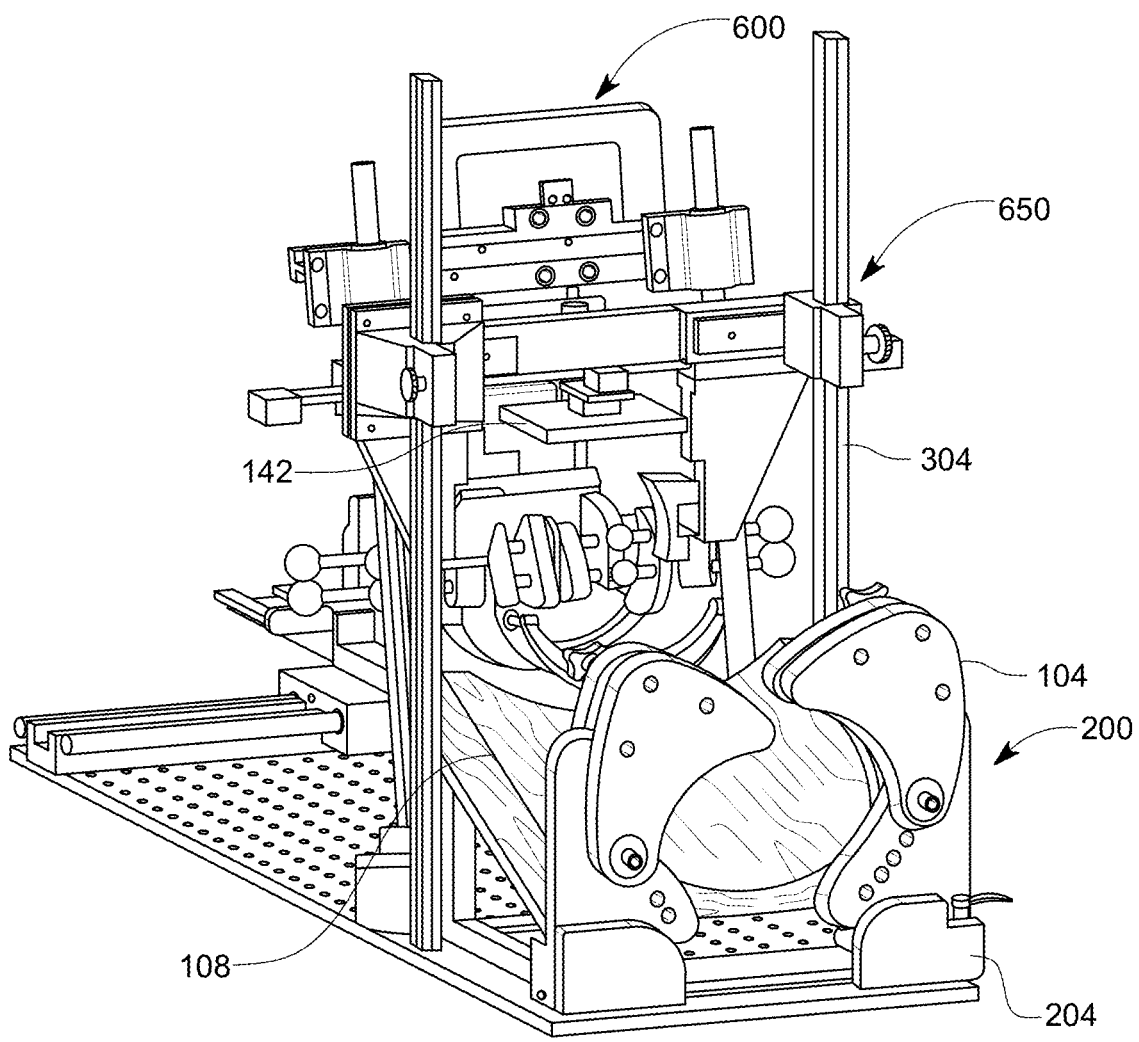
FIG. 4 is a front perspective view of a multi-axial joint laxity testing apparatus as seen from an end carrying a thigh clamshell clamp, according to at least one embodiment.
Figure 5:
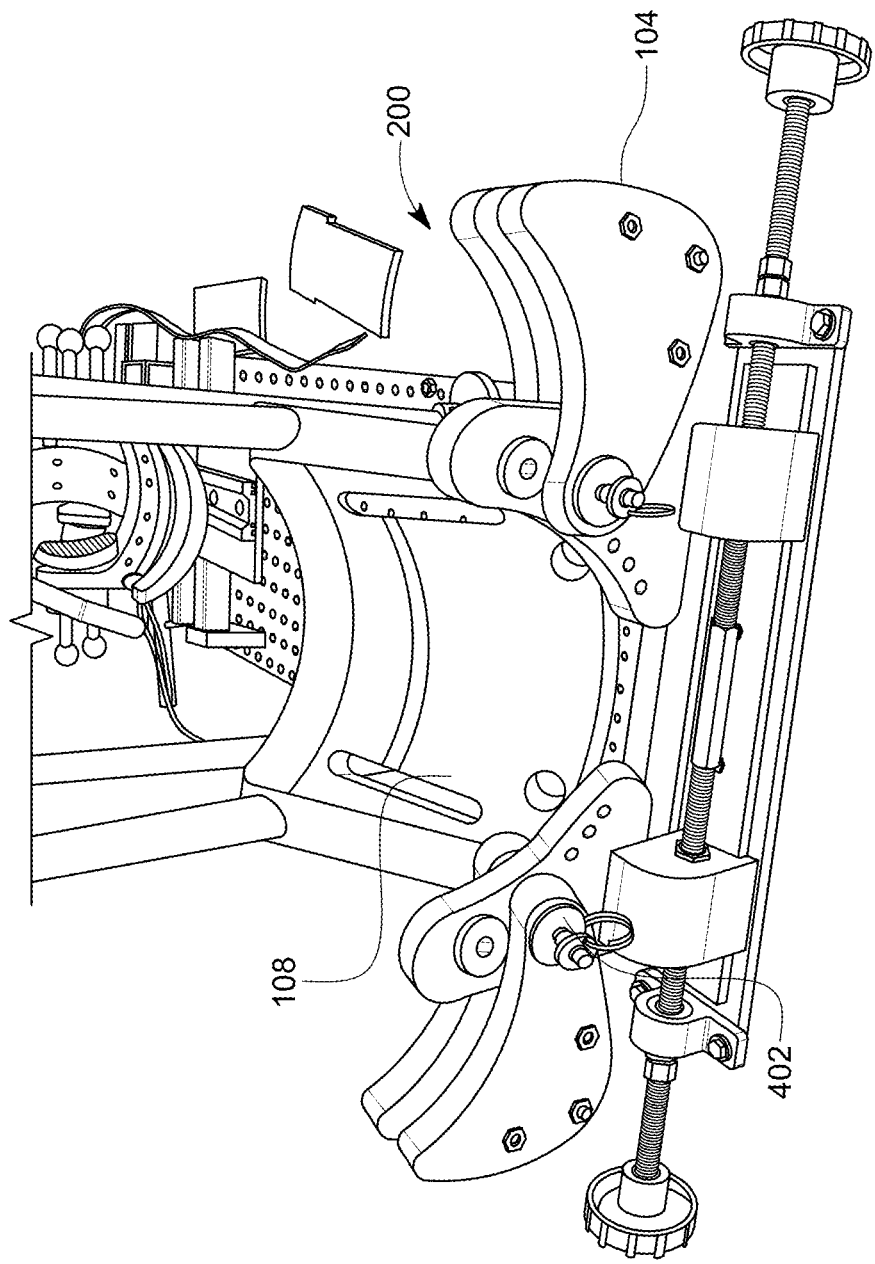
FIG. 5 is a front perspective view of a multi-axial joint laxity testing apparatus as seen from the end carrying a thigh clamshell clamp, according to at least one embodiment.

Proximal thigh fixation module 200 of thigh stabilization assembly 800 includes thigh clamshell clamps 104 that can be adjusted to any width and circumference of the subject's thigh (see FIG. 7 for example) to firmly stabilize the proximal thigh while ensuring patient comfort. Each of two thigh clamshell clamps 104 can be configured to open out and away from each other about a hinge (compare FIG. 4 to FIG. 5). Thigh cradle 108 is adjustable to ensure more consistent positioning of the thigh in the frontal and transverse plane. Thigh clamshell clamps 104 operate as a thigh restraint by way of ensuring consistent positioning of the thigh in the frontal and transverse plane. In one embodiment, proximal thigh fixation module 200 may integrate or otherwise firmly attach distal thigh fixation module 650 with thigh cradle 108. Thigh clamshell clamps 104 can be adjusted at clamshell base 204 to adjust the width to the patient's thigh. The height of the clamps of thigh clamshell clamps 104 can be adjusted via a lock pin 402 that can be inserted into holes at incremental heights for larger and smaller thighs. During operations, to secure a thigh of a patient, clamping arms 202 of thigh clamshell clamps 104 are moved toward each other to "snuggly" fit the contour of the thigh and then held firmly in place by tightening arm knob 218. The two clamping arms 202 are offset so they are able to overlap and ensure custom fit for any size leg. In at least one embodiment, proximal thigh fixation module 200 is accordingly designed to work with the condylar and patella clamps on U-bar assembly 502A to firmly hold the thigh in place while the leg is manipulated during testing. proximal thigh fixation module 200 can include a clamshell base 204 and two clamping arms 202 that are attached at the proximal end of clamshell base 204 just proximal to the thigh cradle 108. In at least one alternate embodiment, clamshell base 204 and two clamping arms 202 are designed to be integrated into the thigh cradle 108. In one embodiment, clamping arms 202 are attached or coupled to a rail system 206 that allows clamping arms 202 to be adjusted in width relative to one another and the patient's thigh. Once the bases of the arms are snug against the posterior medial and lateral aspects of the thigh of a patient, the two clamping arms 202 are then pivoted to wrap around the circumference of the thigh, again, accommodating varying leg sizes (overall dimensions; see FIG. 7). Once positioned to firmly compress and stabilize the thigh, arm knob 218 representing a clamshell knob offers a way to secure each clamp in place with respect to the desired stabilization and comfort of the patient. Clamping arms 202 can also open up and lay flat to ease moving the leg in and out of the device (see FIG. 5).

Thigh cradle 108 can be configured to mirror the natural curvature of the underside of the thigh. In various embodiments, the width may increase slightly from distal to proximal to accommodate the shape of the thigh. The two sliding clamping arms 202 can be configured to come in from medial and lateral sides of the more proximal end (closest to the hip) of thigh stabilization assembly 800 with the condylar clamps and a patella pad being configured to stabilize the thigh on the more distal end of thigh stabilization assembly 800 to firmly fix the thigh in the cradle and further constrain frontal and transverse plane motion of the femur. Proximal and distal are termed used herein with respect to a patient positioned with a leg extending longitudinally from their body from proximal to distal. Thus, the lower end of the thigh cradle 108 extending toward a patient's torso can be described as proximal, and the higher end extending away from the patient's torso and toward the AP loading assembly 600 can be described as distal. In one embodiment, a single thigh strap may be placed at the distal end allowing moderate pressure to be placed on the thigh, thereby compressing it comfortably to help control extraneous thigh movement in the thigh cradle. Along with the shank cradle, it can allow accurate positioning of the knee from 0-30 degrees of flexion. In an alternate embodiment, the single thigh strap is replaced by, or integrated into, a proximal thigh fixation system as described below.

Proximal thigh fixation module 200 can provide for multiple uses. In at least on embodiment, proximal thigh fixation module 200 elevates, positions and comfortably supports the thigh of the leg to be measured so that AP loading assembly 600 and foot and ankle stabilization assembly 400 can be properly interfaced with the leg. In conjunction with AP loading assembly 600 and distal thigh fixation module 650 (distal thigh fixation module 650 includes U-bar assembly 502 that supports patella pad 142 and condyle clamps 144), proximal thigh fixation module 200 can operate to immobilize the thigh to prevent movement during laxity testing (manipulation of the tibia/fibula relative to the fixed femur). In equipment existing in the market today, the thigh is positioned on a bolster to place the knee at approximately 25 degrees, the bolster typically being a flat piece that does not control in any way for thigh rotation. By contrast, proximal thigh fixation module 200 of apparatus 100 includes a shaped thigh cradle 108 and further includes thigh restraint/strapping systems to ensure more consistent positioning of the thigh in the frontal and transverse plane.

Thigh cradle 108 can operate to reproducibly position and securely hold the patient's thigh during measurement. The thigh cradle is affixed to base 102 such that it cannot move during measurement or otherwise contribute to a patient fall from the standard treatment table. The thigh cradle can be alternately affixed to the device base, with the device base being firmly affixed to a standard treatment table. The patient may be upon a chair in the fowler's position or on a standard treatment table in a supine position and the patient's leg is placed atop thigh cradle 108. Thigh cradle 108 may be high enough to allow for any relevant components to reside underneath it, but not so high that the patient's hips are unseated from the chair. Thigh cradle 108 may also angled in such a way to allow for testing to be completed with a knee angle of approximately 0-30 degrees when measured from full extension (see FIG. 1, for example). The patient's thigh is secured to the thigh cradle in a manner that requires 1 minute or less by the end user.

Figure 3:
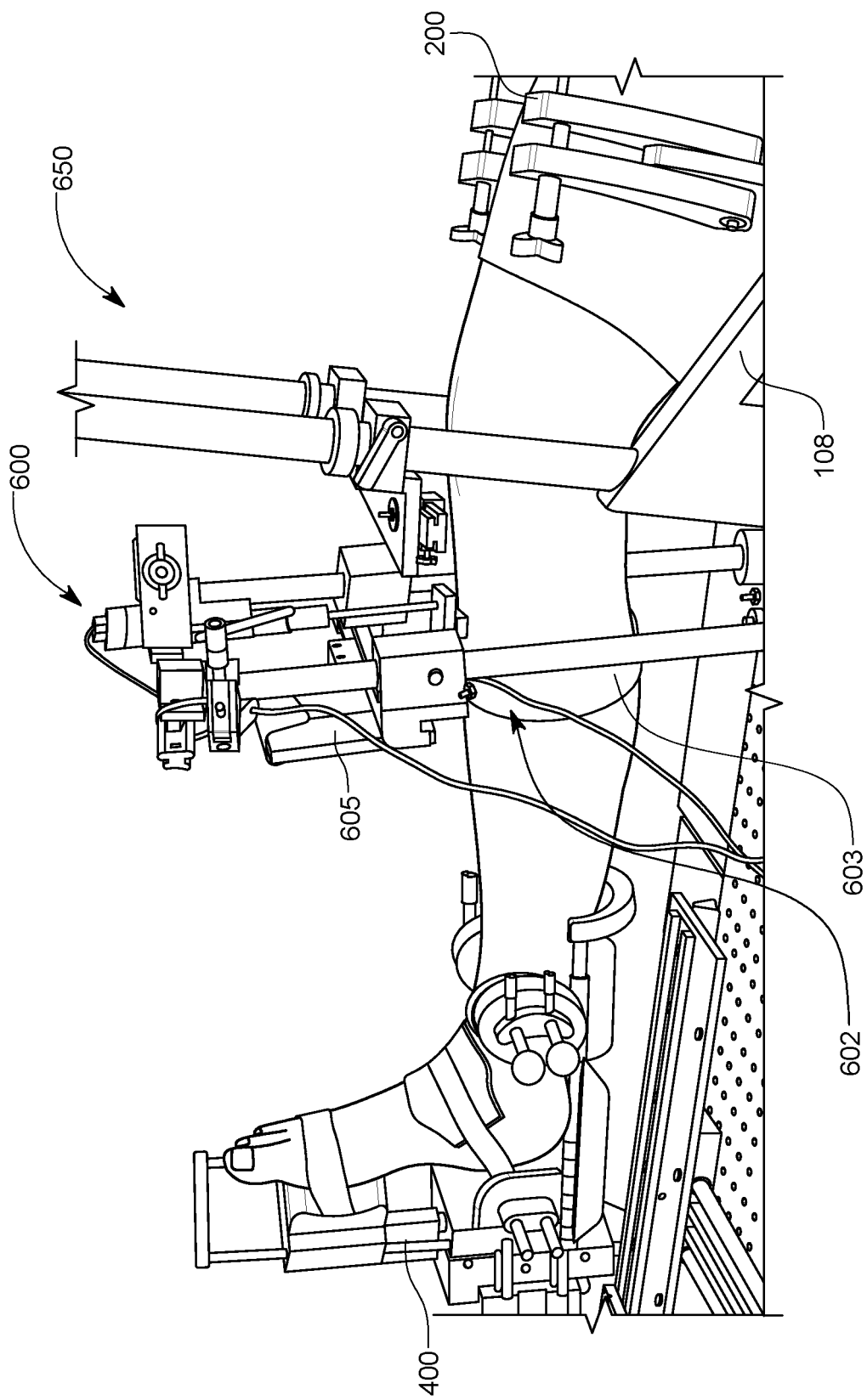
FIG. 3 is a side perspective view of a multi-axial joint laxity testing apparatus with the leg of a person secured therein for anterior-posterior knee laxity testing purposes, according to at least one embodiment.
Figure 6:
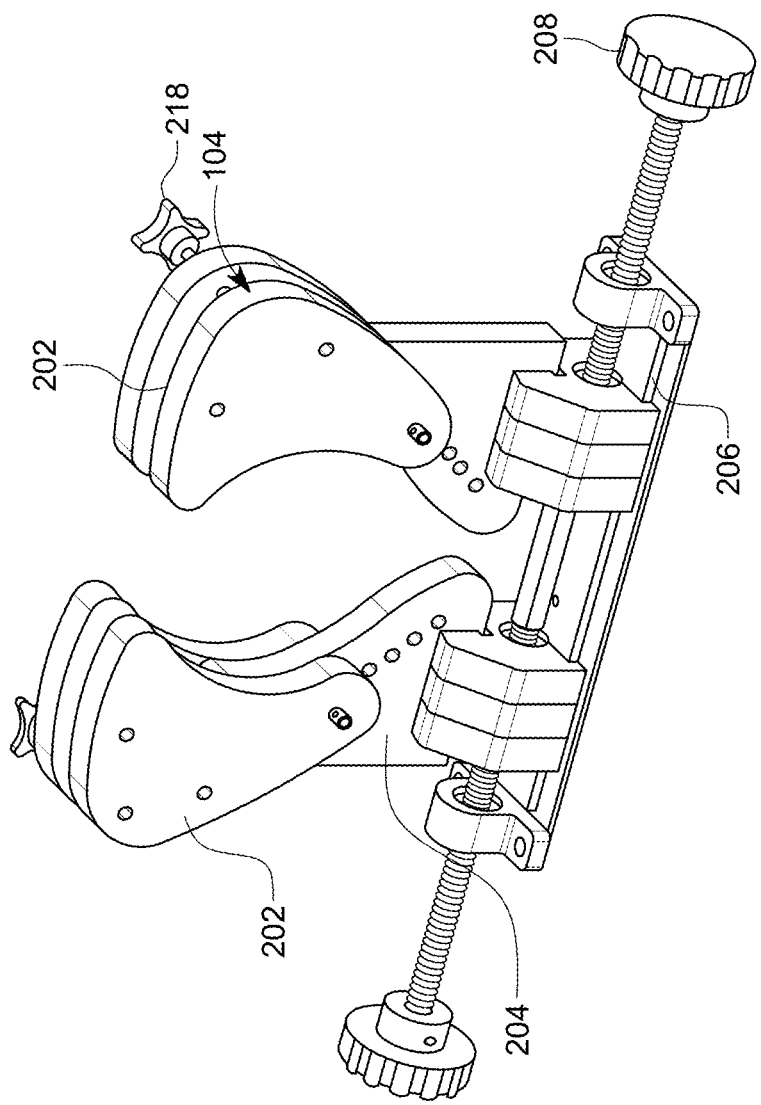
FIG. 6 is a perspective view of a thigh clamshell clamp forming part of the multi-axial joint laxity testing apparatus, according to at least one embodiment.
Figure 7:
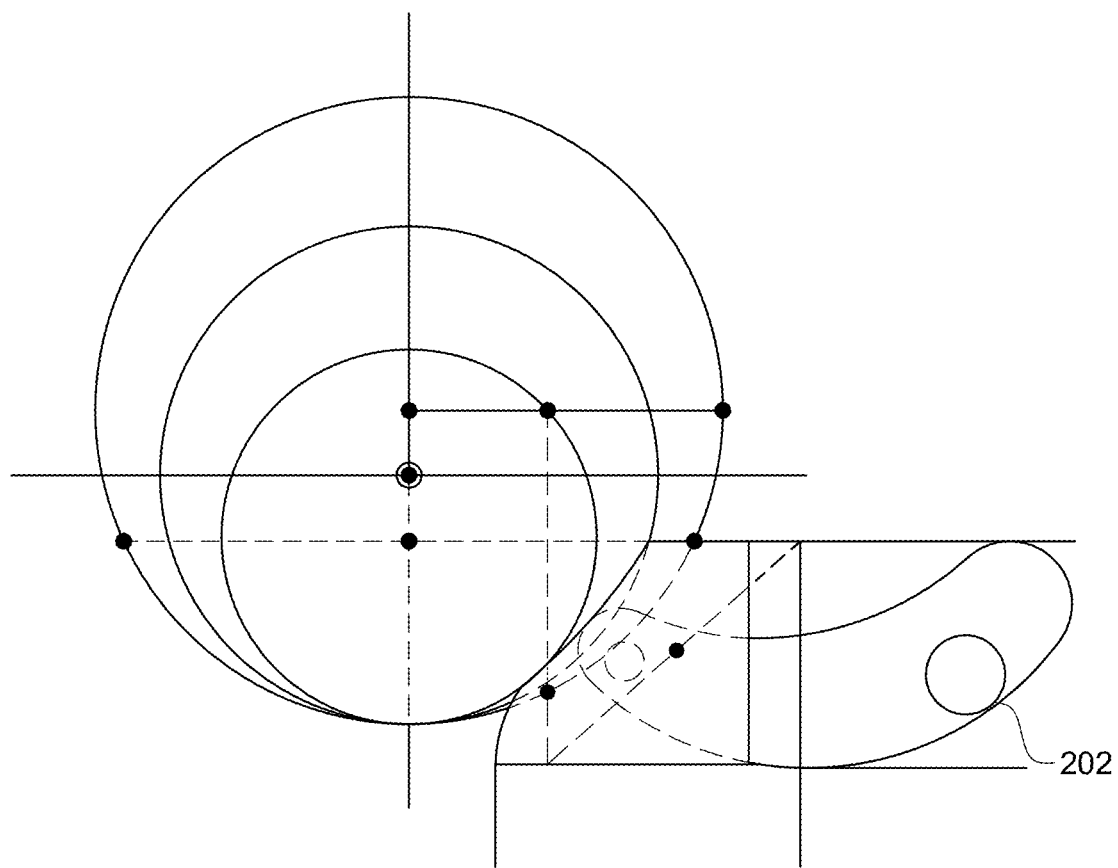
FIG. 7 is a plan view of a thigh clamshell clamp forming part of a multi-axial joint laxity testing apparatus with thighs of various diameters juxtaposed thereto, according to at least one embodiment.
Figure 8:
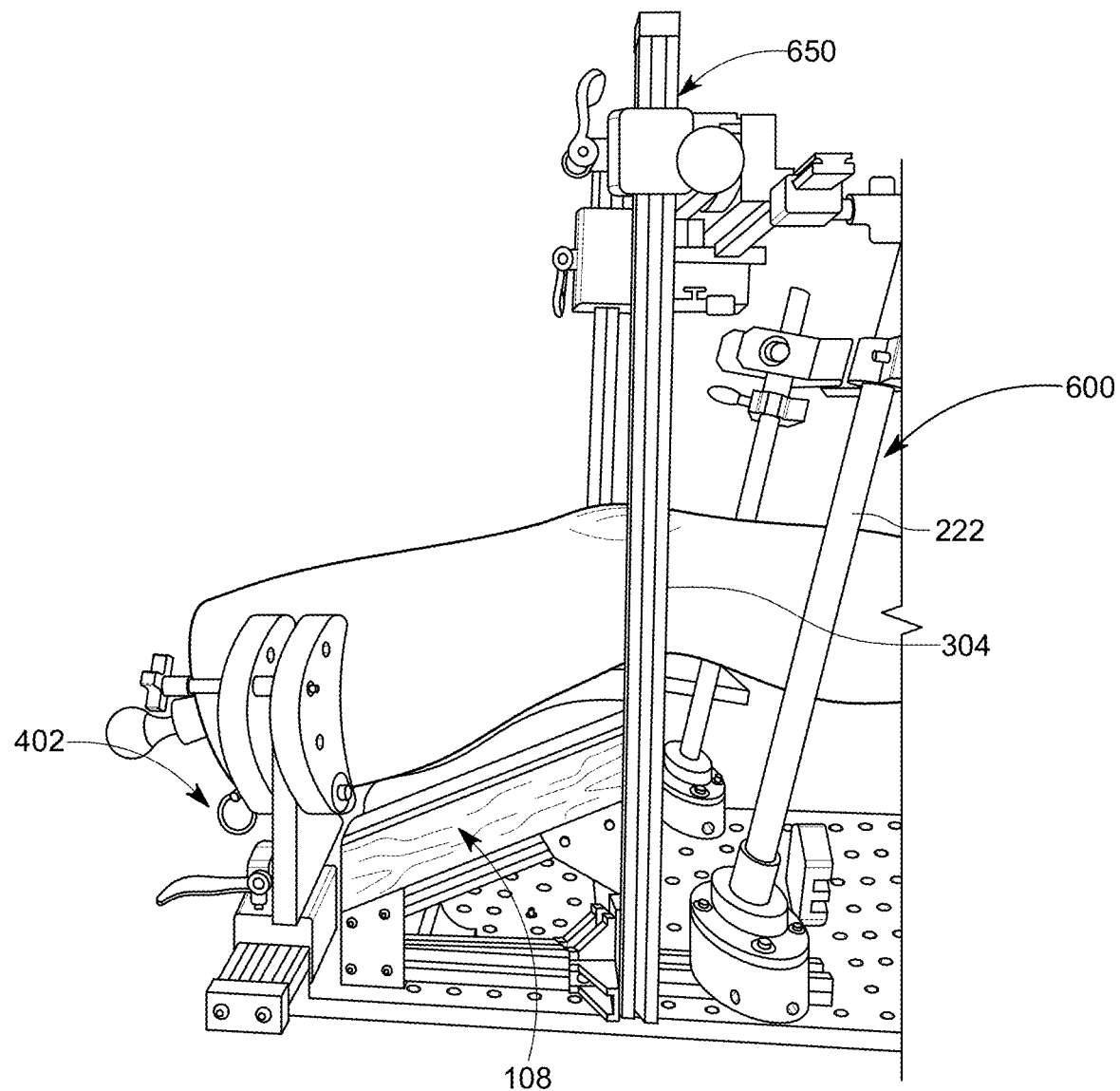
FIG. 8 is side perspective view of a multi-axial joint laxity testing apparatus with the thigh of a prop placed therein, according to at least one embodiment.
Figure 9:
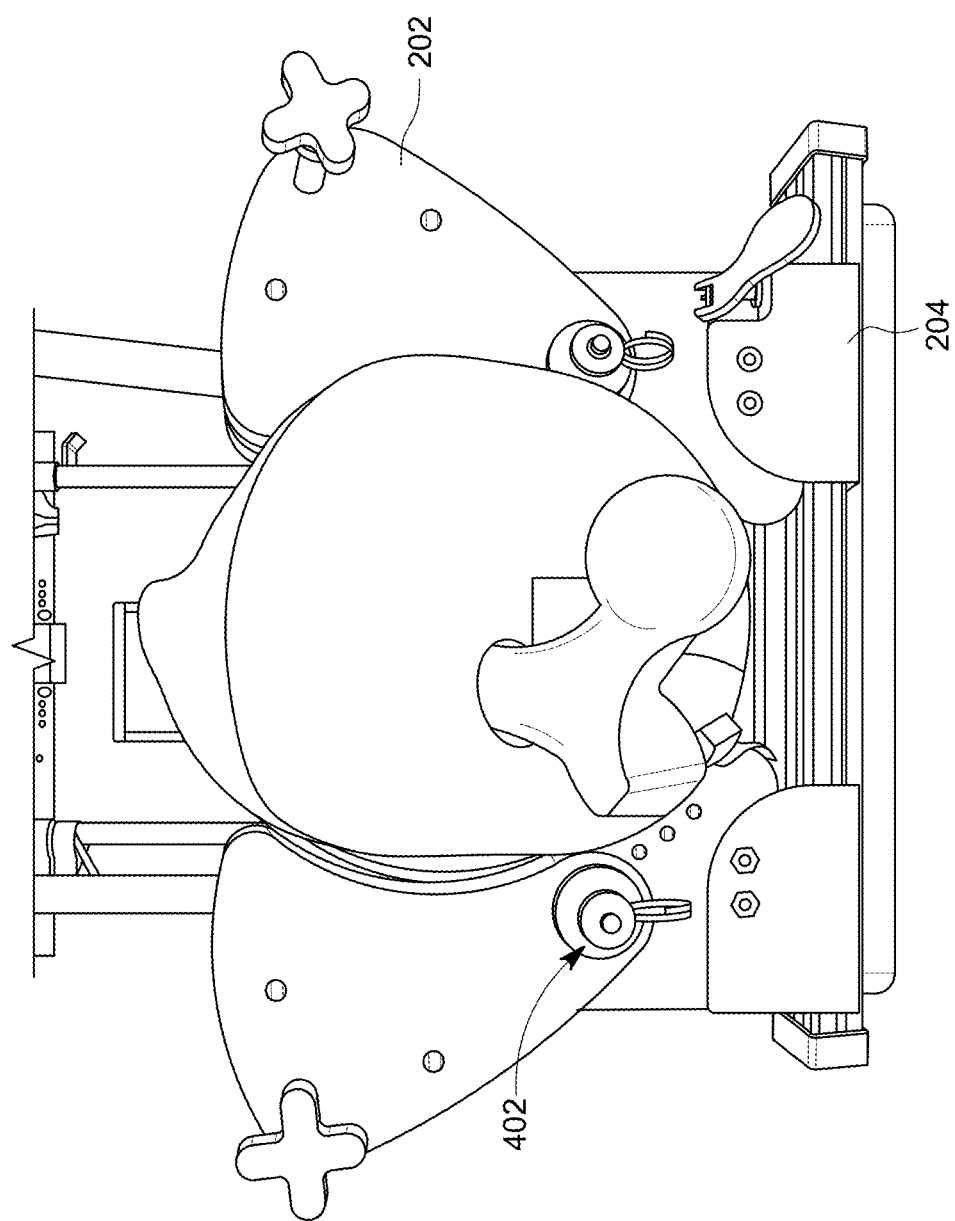
FIG. 9 is a front perspective view of a multi-axial joint laxity testing apparatus as seen from the end carrying a thigh clamshell clamp with the leg of a prop secured therein, according to at least one embodiment.
Figure 10A:
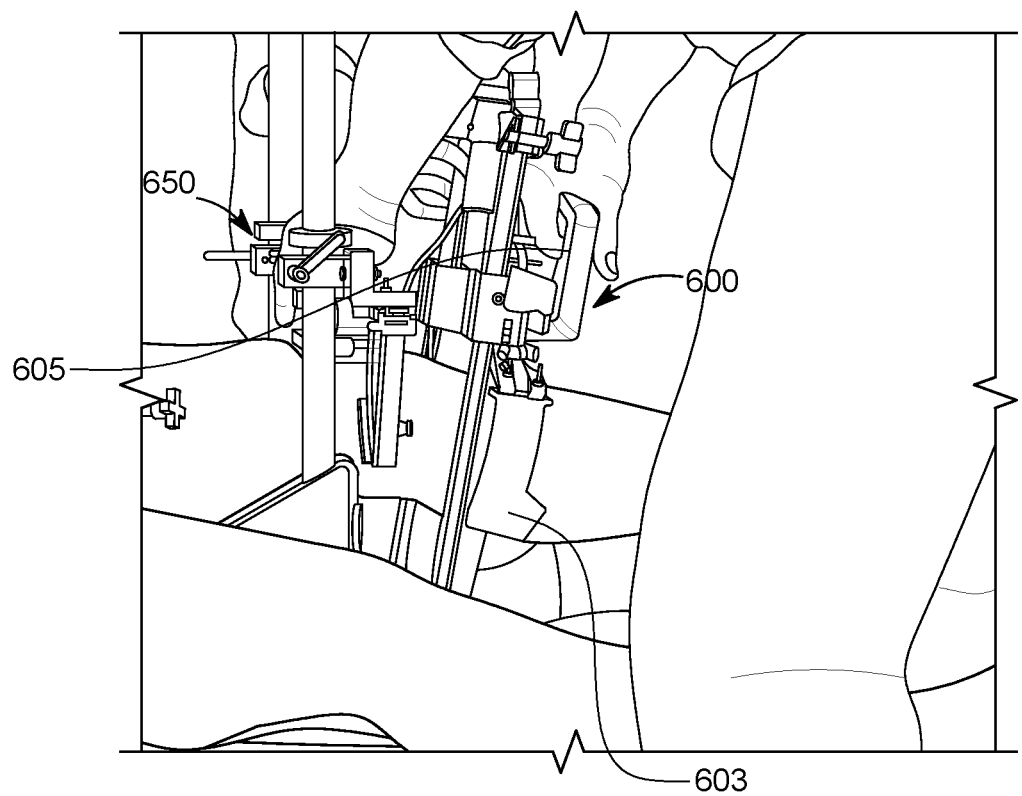
FIG. 10A is a side perspective view of a multi-axial joint laxity testing apparatus with the leg of a person secured therein and being tested for anterior-posterior knee laxity, according to at least one embodiment.
Figure 10B:
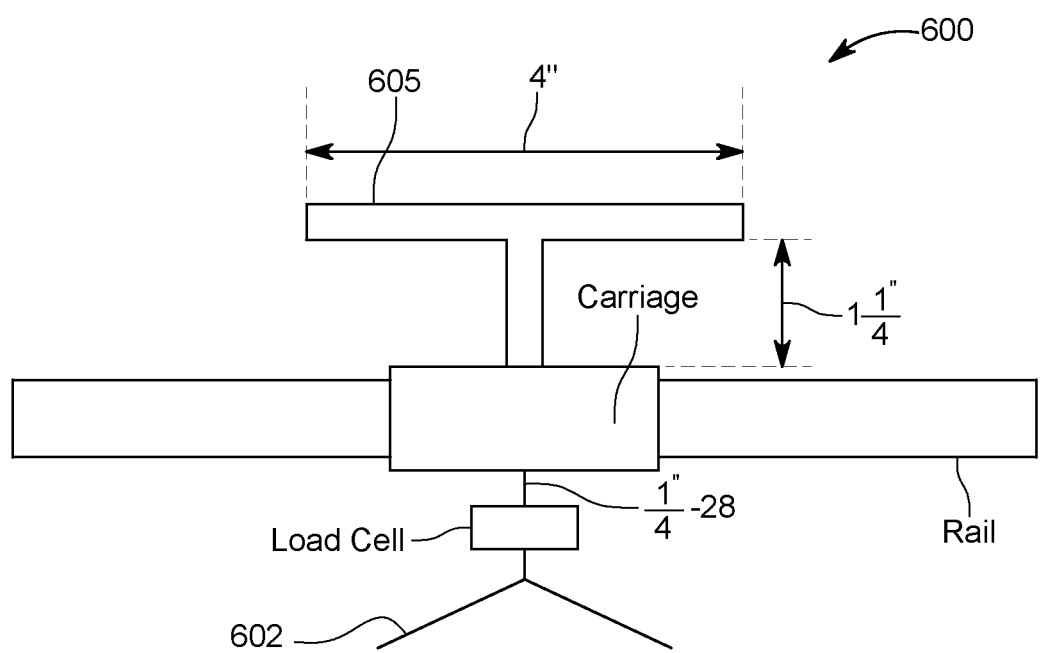
FIG. 10B is a plan view of a portion of an AP loading mechanism of a multi-axial joint laxity testing apparatus, according to at least one embodiment.
Figure 14:
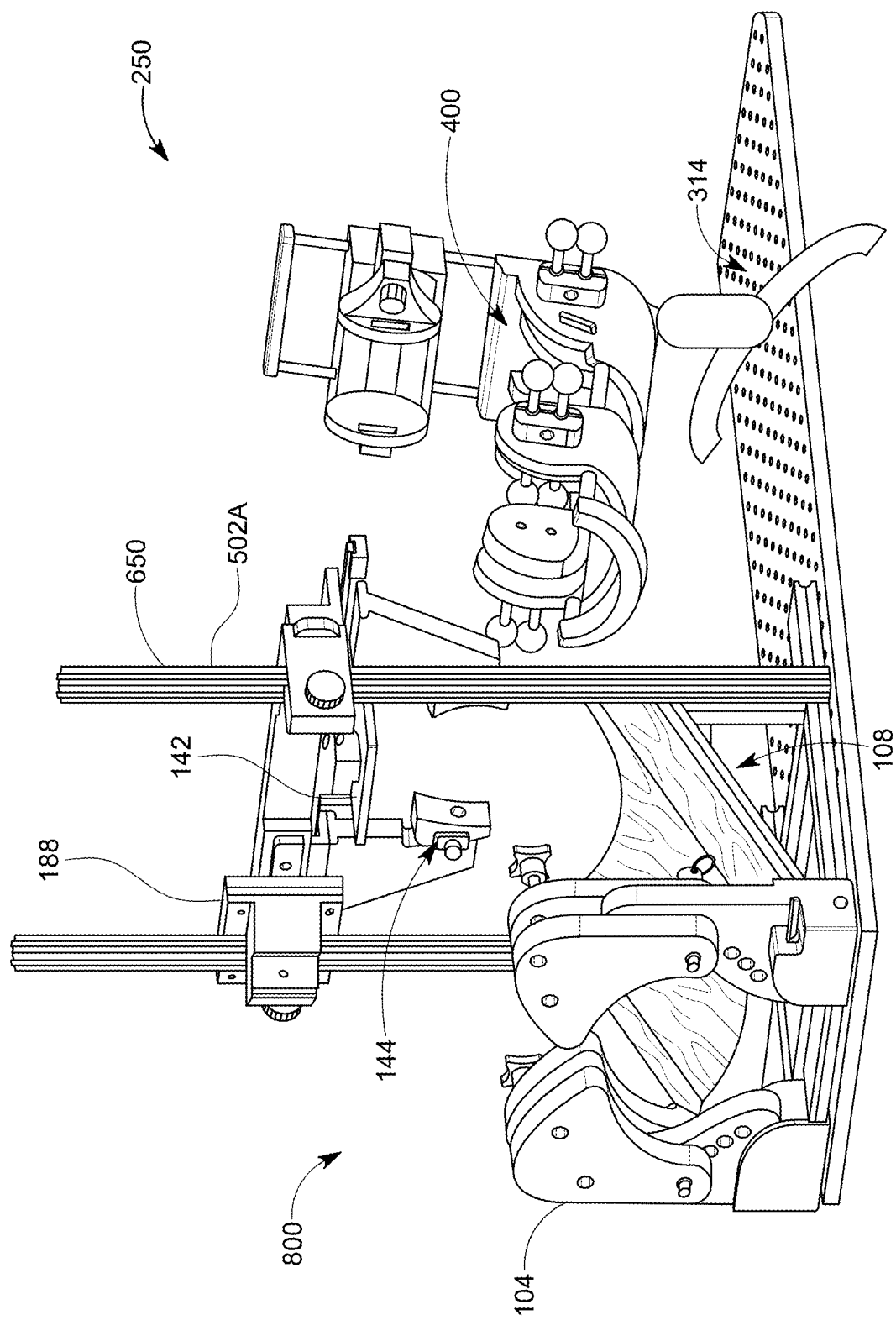
FIG. 14 is a side perspective view of a varus-valgus laxity module forming part of a multi-axial joint laxity testing apparatus, according to at least one embodiment.
Figure 15:
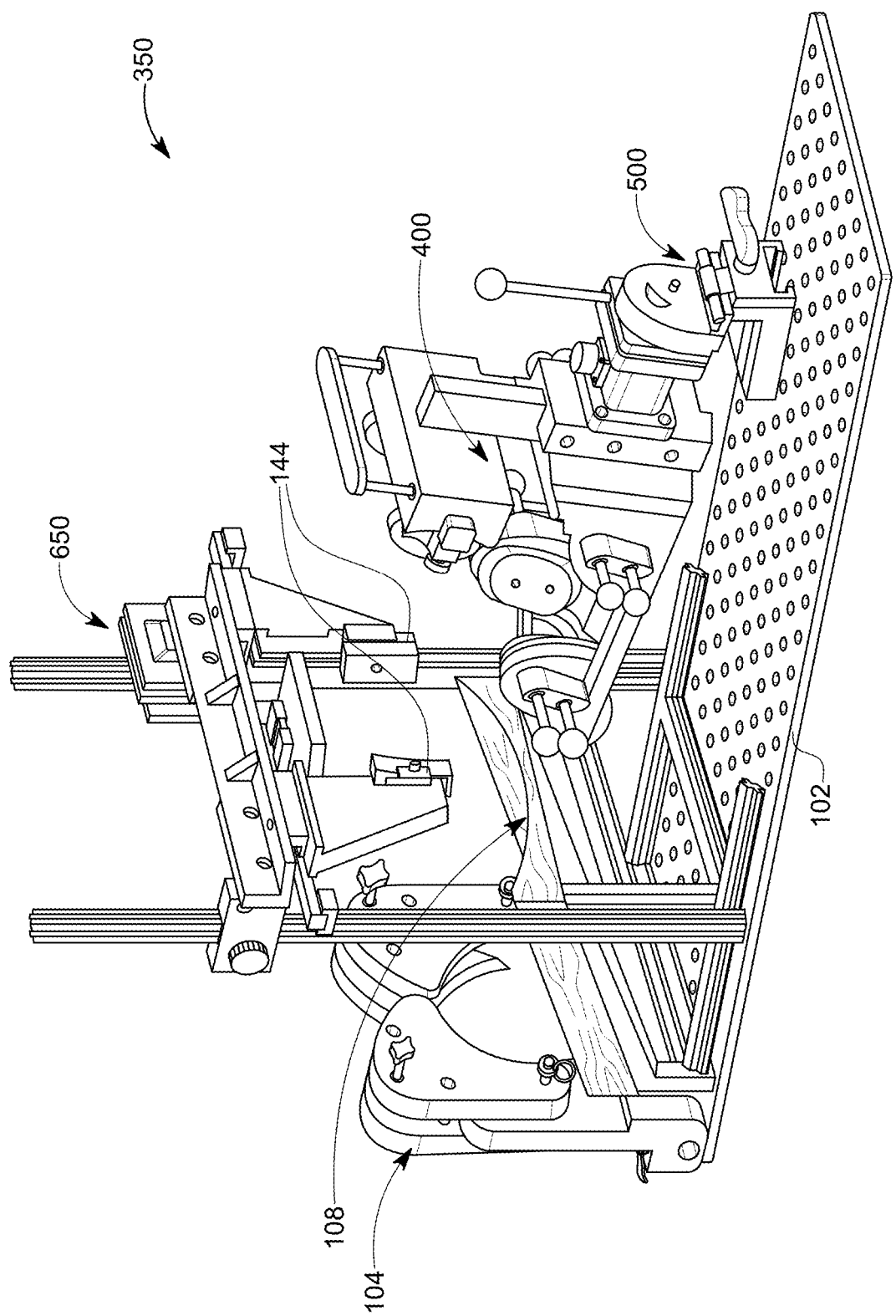
FIG. 15 is a side perspective view of an internal-external rotation laxity module forming part of a multi-axial joint laxity testing apparatus, according to at least one embodiment.
Figure 16:
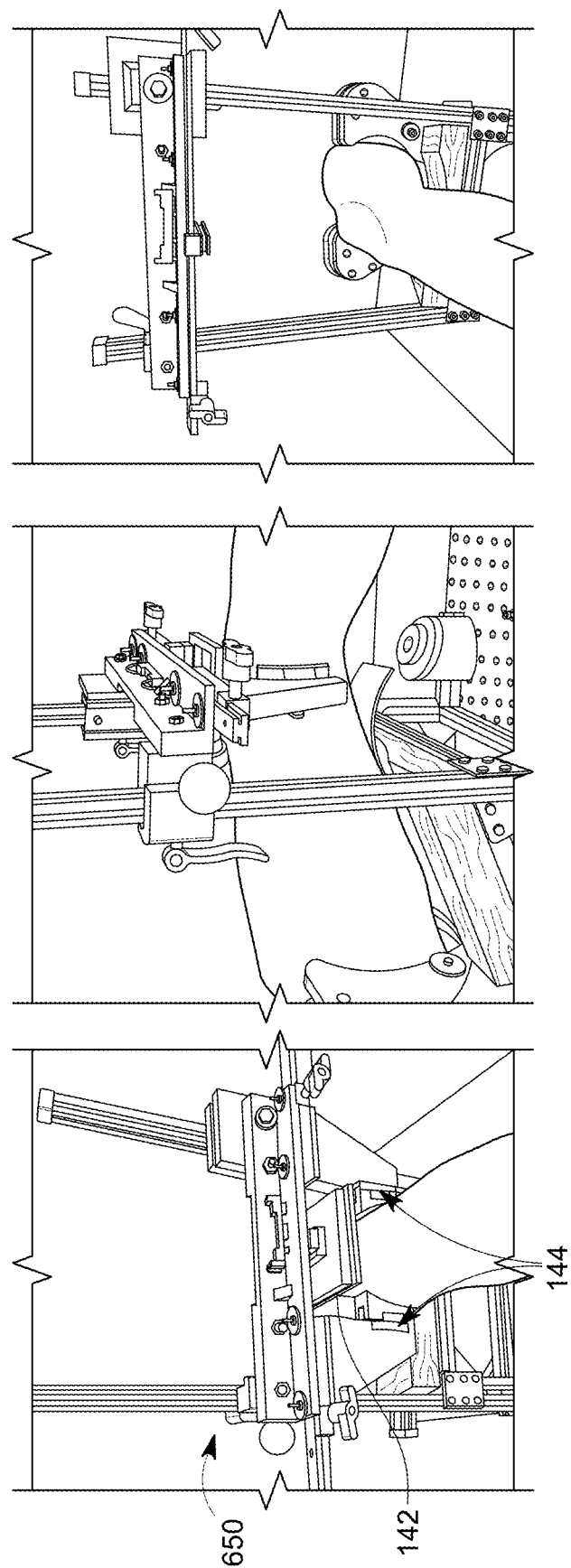
FIG. 16 is a side perspective view of a distal thigh stabilization system with the two condylar clamps and patella pad forming part of a multi-axial joint laxity testing apparatus with the leg of a person secured therein and being tested, according to at least one embodiment.

AP loading assembly 600 operates as an anterior-posterior knee laxity loading mechanism. AP loading assembly 600 is positioned between proximal thigh fixation module 200 and foot and ankle stabilization assembly 400. Anterior-posterior displacement of a patient's knee joint in the sagittal plane can be achieved manually with AP loading assembly 600. AP loading assembly 600 is located at the proximal tibia/fibula (see FIG. 3). As illustrated in FIGS. 10A and 10B, AP loading assembly 600 includes handle 605 in line with load cell and tibial plate 602 that is attached to a horizontal bar and circular bearings that to be guided along two rails in line with a joint line. In one embodiment, handle 605 is in line with proximal tibial plate 602 that is strapped to the patient's proximal tibia/fibula with a strap 603 (see FIG. 10A). The handle may be attached to a horizontal bar that has circular bearings at each end so that the handle is guided along two rigid bars such as vertical bars 222 to standardize direction of force application to achieve anterior-posterior translation of the tibia/fibula on the femur (see FIG. 10B). In various embodiments, the inclination of the guide rails can be adjusted to ensure direction of load application is aligned parallel to the joint line and ensures that every tester or clinician applies AP load in a same manner. The two clamping arms 202 coupled to proximal thigh fixation module 200 proximally along with distal thigh fixation module 650, operate to secure a thigh positioned on thigh cradle 108. FIG. 6 illustrates thigh clamshell clamps 104. FIG. 7 illustrates the ability of clamping arms 202 of thigh clamshell clamps 104 to swivel away to allow ease of movement of the limb/thigh in and out of apparatus 100. FIGS. 14 and 15 illustrate distal thigh fixation module 650 that includes two condylar clamps and a patella stabilization pad. In some embodiments, the vertical bar can swing away for ease in positioning a patient in the device.

In various embodiments, AP loading assembly 600 may operate to only provide anterior/posterior loading, with the stabilization of the tibia/fibula being performed by foot and ankle stabilization assembly 400. In at least one embodiment, a single linear rail may be utilized for allowing for varus/valgus (VV) movement. According to one or more embodiments, AP loading assembly 600 comprises an actuated linear mechanism for providing an anterior-posterior (AP) loading. AP loading assembly 600 for AP testing can include an A/P actuator apparatus. In some embodiments, foot and ankle stabilization assembly 400 interfaces with the proximal lower leg so that anterior/posterior translational laxity tests may be performed. By using the force actuator(s), the weight of the limb of a patient can be determined prior to testing so that load can be offset that load to achieve a neutral, zero-shear load starting position from which to determine anterior displacement and posterior displacement from this zero-reference position. The interface between AP loading assembly 600 and the leg can include thigh cradle 108 of proximal thigh fixation module 200, patella pad 142 and condyle clamps 144 of distal thigh fixation module 650, and posterior leg support 210 of foot and ankle stabilization assembly 400, each of which may be padded. To perform posterior testing a tibial plate 602 may provide compression over the top of the shank while a wraparound strap 603 provides compression for anterior testing. Tibial plate 602 may be non-elastic. Apparatus 100 is configured for manual loading as well as automated/robotic loading.

AP loading assembly 600 is configured for applying anterior-to-posterior and posterior-to-anterior directed load to the proximal shank (with the thigh stabilized) in a manner similar to a manual Lachman's test. AP loading assembly 600 can include, in at least one embodiment, at least 2 cm of action (see data provided in Table 1 further below in this document). AP loading assembly 600 can apply anterior directed loading (pulling) and posterior directed loading (pushing) to the proximal shank through the tibial plate and calf strapping system that interfaces with the proximal shank and enables the shank to be manipulated both anteriorly and posteriorly. In at least one embodiment, the goal is to apply up to 150 N anterior directed loads and 100 N posterior directed loads. A potentiometer or similar measurement device affixed at the tibia/fibula tuberosity can operate to measure relative displacement of tibia/fibula relative to the patella (femur). In the same embodiment or in a different embodiment, the goal may further comprise applying a fixed load and measuring the displacement at that load. The measured displacement is analogous to what is written for VV and IER below.

Distal thigh fixation module 650 includes U-bar assembly 502 that supports patella pad 142 and condyle clamps 144 (see FIG. 14). Each condyle clamp 144 has a downward extending end upon which a respective condyle clamp 144 (see FIG. 15) is mounted. AP loading assembly 600 is removed in FIG. 15 and both AP loading and distal thigh fixation is removed in FIG. 2 for illustration purposes. In one embodiment, patella pad 142 is mounted to a linear sliding track that is also mounted to the underside of U-bar assembly 502. A condyle pad adjustment arm may extend from and are adjustable relative to the U-bar assembly 502. The condyle pad adjustment arm may have on its medial face a rubberized condyle pad. Each of the two arms/faces may be guided by a fully supported linear clamping mechanism which allows for quick-release and fine adjustment by flipping the release valve or squeezing the adjustment trigger, respectively. The adjustment feature allows the condyle pads to be more adjustable to accommodate for a greater number of condylar widths and heights and configurations. U-bar assembly 502 houses and supports patella pad 142 and a condyle clamping system that includes condyle clamps 144. Patella pads 142 may be further configured to be able to adjust up and down for different condylar heights, for example using adjustments 188 and condyle clamps 144, to thereby accommodate different size knees. U-bar assembly 502 is supported by and spans two vertical height adjustment bars 304 (see FIG. 4) approximately between which a patient's knee will be placed in use with the patella pad 142 (see FIG. 4) positioned above the patella of the knee. In one embodiment, U-bar height adjustment clamps are provided at lateral ends of U-bar assembly 502 to permit vertical movement of the U-bar assembly 502 along the vertical height adjustment bars 304 to a preferred height and then fixation of the U-bar assembly 502 by use of U-Bar height adjustment clamps. The two condyle clamps 144 may be carried by the U-bar assembly 502. Condyle pad adjustment arms may be adjustably connected to the U-bar assembly 502 by way of condyle pad clamps. By interfacing with two vertical height adjustment bars 304 attached to the base 102, U-bar assembly 502 is able to snug up to the patella and the medial and lateral femoral condyles of the leg being examined and fix itself, compressing and immobilizing the patella in the femoral intercondylar groove and preventing extraneous motion of the femur during testing.

Together, patella pad 142 (see FIG. 14) and condyle clamps 144 (see FIG. 14) can operate to stabilize the femur in the thigh cradle, preventing movement of the femur during anterior-posterior (AP), varus-valgus (VV) and internal-external rotation (IER) testing. U-bar assembly 502 is accordingly designed for superior fixation of the femur. To test multiple planes in a single apparatus and patient positioning, stabilization of the thigh is needed such that it remains fixed, whether applying loads in sagittal, frontal or transverse planes. U-bar assembly 502 can operate to stabilize the contoured patella pad 142 that seats the patella in the femoral groove to thereby stabilize the femur during AP testing. Condyle pads and condyle pad adjustment arms may also be provided as part of U-bar assembly 502. Condyle pads are designed to work together to provide a counterforce against loads in the frontal and transverse plane. Used with patella pad 142 and the rest of thigh stabilization assembly 800, the counterforces created by condyle pads can operate to stabilize the thigh during frontal and transverse plane loading of the tibia/fibula. Condyle pad adjustment arms may be held parallel to the body of the U-bar such that when they are extended the condyle pads will lie approximately 3.8 cm away from the center of the patella pad 142. Condyle pad adjustment arms are linearly extensible shafts that, on their lower ends, interface with the condyle pads. Each of the two shafts is inserted through a sheath that guides the shaft and allows for angular articulation. The condyle pads may operate to slide in to accommodate different widths and slide up and down to accommodate different heights. In other words, the condyle pads will slide in to accommodate different widths and slide up and down to accommodate different heights. U-bar assembly 502 can accordingly deploy the condyle pads, which interface the distal condyles of the femur to the U-bar set up. Condyle clamps 144 may be lockable so that the position can be maintained during testing. When the clamps are engaged, condyle clamps 144 operate to snug the condyle pads up against the medial and lateral condyles of the subject to prevent frontal and transverse plane movement of the proximal thigh during testing. This, together with the proximal clamping arms on the thigh cradle pads, ensures that the femur is firmly fixed for testing.

The condyle pads can provide a comfortable, yet rigid interface between the thigh fixation system and the patient's medial and lateral distal femoral condyles to prevent femoral movement during VV and IER testing. The condyle pads can be contoured such that they interface with the rounded condyles of the distal femur. The surface of the contoured pad can coated with a substance that is firm, pliable and tacky (e.g., silicone rubber) so as to promote a secure interface between the rigid body of the pad and the condyles.

In at least one embodiment, condyle clamps 144 may be attached to and guided by a respective condyle pad adjustment arm. Patella pad 142 may be mounted to a linear track on an underside of the U-bar assembly 502 or U-bar assembly 502A. U-bar assembly 502 or U-bar assembly 502A can include a U-bar adjustably mounted upon vertical height adjustment bars. U-bar assembly 502 or U-bar assembly 502A may further include a swing arm whereby U-bar assembly 502 or U-bar assembly 502A may swing away from the leg, making it easier to place the extremity into the device. In at least one embodiment, patella pad 142 has a flat surface that represents a moldable deforming surface that interfaces with the shape of the patella to improve comfort. In various embodiments, the patella pad includes a cushioned, deformable, and/or resilient flat surface which interfaces with the patient's patella to increase comfort and conformity to varying patellar shapes.

According to various embodiments, patella pad 142 operates to seat the patella of the subject within the femoral intercondylar groove by applying compression to the patellar bone when the leg is in approximately 20-30 degrees of flexion. According to some embodiments, patella pad 142 may not be contoured and instead be in the form of a flat pate so that it can accommodate all the different size patella. In other words, patella pad 142 may be contoured in some embodiments and may not be contoured in other embodiments. Accordingly, in at least one embodiment, patella pad 142 can be flat on its interfacing edge. This design can compress the patella and allow maximal flexibility in a range of patient shapes/sizes. In at least one embodiment, patella pad 142 can include a rubberized surface that interfaces with a patient's patella to increase comfort and conformity to varying patellar shapes. Furthermore, patella pad 142 is connected to U-bar assembly 502 at an adjustable distance to create a rigid point of contact through which compression may be applied by adjusting the position of U-bar assembly 502 along vertical height adjustment bars 304. Patella pad 142 can also be configured to be adjustable in the medial and lateral direction to ensure proper alignment and compression of the patient's patella once properly positioned in thigh cradle 108.

In the illustrated embodiment of FIG. 1, U-bar assembly 502 of distal thigh fixation module 650 is mounted on vertical adjustment or riser bars in the form of vertical height adjustment bars 304 that arise from the thigh cradle for stability. In some embodiments, AP loading assembly 600 is mounted, by way of vertical bars 222, on base 102 independently from thigh stabilization assembly 800, which may mounted on base 102 by riser bars interconnected by a base-end bracket.

In the illustrated embodiment of FIG. 1, distal thigh fixation module 650 and proximal thigh fixation module 200 are mounted together upon the same vertical adjustment or riser bar assembly defining a more consolidated set up. In some embodiments, U-bar assembly 502 of distal thigh fixation module 650 may be mounted, by way of vertical height adjustment bars 304, on base 102 independently from proximal thigh fixation module 200, which may mounted on base 102 by riser bars interconnected by a base-end bracket.

Foot and ankle stabilization assembly 400 (see FIG. 1) operates to secure the lower limb so that force application from heel and linear slide 500 can be effectively transferred into the lower limb. According to some embodiments, both Internal-External (IE) rotation and varus-valgus rotation laxity tests can have their load application through heel and linear slide 500, so it must have a snug interface with the patient's ankle and foot. In some alternate embodiments, the load application can occur from the proximal region. Foot and ankle stabilization assembly 400 represents the tibia/fibula, ankle and foot fixture. The foot and ankle stabilization assembly 400 acts as a virtual extension of the patient's leg, maximizing force transfer to the patient's lower leg, ensuring accurate and reliable force transfer ultimately minimizing measurement error. In one embodiment, foot and ankle stabilization assembly 400 comprises an actuated track upon which a carriage is mounted. However, this feature is optional in that in some embodiments, foot and ankle stabilization assembly 400 does not include an actuated track. Foot and ankle stabilization assembly 400 operates to secure the foot, ankle and lower leg such that it moves as one unit to reduce movement artifact. Foot and ankle stabilization assembly 400, much like thigh stabilization assembly 800, is designed to control and standardize the amount of tibia/fibula rotation, which can have a significant impact on laxity measurements. Foot and ankle stabilization assembly 400 is configured to be adjustable in the transverse plane so that the tibia/fibula can be positioned such that the tibiofemoral joint is in neutral rotation, and then locked in this neutral orientation during AP and VV testing for accurate and repeatable results. In some embodiments, foot and ankle stabilization assembly 400 may at least partially resemble an orthopedic walking boot in some embodiments and may have a series of clamps at the foot, ankle, and lower leg. To accommodate various shank (tibia/fibula) lengths, the distal attachment of the footplate can be extendable by moving VV carriage 606 in a distal-proximal direction that is roughly perpendicular to VV track 604. Foot and ankle stabilization assembly 400 can be extended to the correct length, then locked in place so that it remains rigid during testing. This component itself can also be rigid to avoid bending during V/V and VE testing.

Foot and ankle stabilization assembly 400 serves as an interface for varus-valgus (VV) rotation actuation. An actuated VV track 604 lies perpendicular to the long edge of the base 102. The VV track 604 represents a horizontal track that allows the tibia/fibula to move in varus-valgus directions. The track may be actuated, for example by an integrated stepper motor forming part of heel and linear slide 500, which allows for precise movement control. The track may controls a carriage, which represents a platform that allows for foot and ankle stabilization assembly 400 and other components to be fastened to it. It should be noted that varus-valgus loads could also be applied manually along the track.

The VV interface can actuate the lower leg tibia/fibula from its distal end (via foot and ankle stabilization assembly 400) in a curvilinear motion whose radius corresponds to that of the leg being measured. This will allow the lower limb to move in a natural arc as the tibia/fibula is rotated relative to the femur in the frontal plane. The design allows this arc to be adjusted to each individual's leg length so that there is no binding or compression at the tibiofemoral joint that would impede laxity testing. This provides greater comfort and relaxation for the patient, and thus a more accurate and repeatable measurement of laxity. Heel and linear slide 500 is directly attached to VV carriage 606. The linear track allows foot and ankle stabilization assembly 400 to move in varus-valgus direction.

Actuated VV track 604 is used to deflect the knee approximately 30 degrees, 15 degrees to each side (see data in Table 1). This will be different for each person and it represents the maximum displacement expected—the goal is to apply a 0-10 Nm torque and measure the amount of displacement, rather than move to a specific displacement. The VV track 604 is a linear track with driver. Perpendicular to this track, attached to the VV carriage 606 is the heel and linear slide 500 that is unactuated, low friction, and lockable. This piece is to be used to adjust the VV actuator for varying leg size. To create an arc from this linear motion an additional low friction track may be used in parallel to the aforementioned one to allow for natural movement of the limb along its arc radius. Heel and linear slide 500 permits length adjustment, and the VV carriage 606 is laterally movable along VV track 604 by the VV track actuator (i.e., the aforementioned stepping motor in at least one embodiment). In some alternate embodiments, the VV carriage 606 is laterally movable along VV track 604 manually by the clinician, for example. Foot and ankle stabilization Assembly 400 includes a fixture that serves as mount and rotational system which holds foot and ankle stabilization Assembly 400 in place and allows for rotational tests to be conducted via a lockable/unlockable pin (so that it can be locked during VV and AP Loading and unlocked during IE loading). IE rotational fixture is attached directly to the VV carriage 606 and separately to heel and linear slide 500. In at least one embodiment, IE rotational fixture of Foot and ankle stabilization assembly 400 is mounted on the carriage via a linear track, thereby facilitating varus-vargus laxity testing.

Accordingly, in various embodiments, thigh stabilization is accomplished by proximal thigh fixation module 200 and distal thigh fixation module 650. The combination works in conjunction with thigh cradle 108 to ensure that the patient's distal thigh does not shift during the measurement operation of the product. This is advantageous, as system 700 and/or apparatus 100 will measure displacement of the lower leg relative to the affixed thigh. The fixture is properly positioned by the end user on three anatomical points of the patient's distal femur: the patella, lateral epicondyle and medial epicondyle. Properly positioned, the fixture is then adjusted to the patient such that sufficient force is applied to the patella and epicondyles to stabilize the thigh without causing pain or injury to the patient. The footplate connector is then fastened to the end of the rotary shaft using tibial clamp 216 and heel clamp 214 such that the shaft (axis of rotation) is collinear to the tibia/fibula of the measured leg, when positioned correctly. The IE actuator may rotate through the long axis of foot and ankle stabilization assembly 400—available range can be at least 50 degrees and may be 60 degrees (see data in Table 1). In at least one example, the IE actuator can be a stepper motor able to create at least 0-5 Nm of torque about its axis of rotation and may have at least a plurality of steps.

Prior to testing, the leg and thigh are to be stabilized within cradle setups that conform to or approximately match the contour of the thigh to firmly stabilize the thigh to the thigh cradle 108, and to the foot and ankle to firmly stabilize in the foot and ankle stabilization assembly 400 so that when the thigh cradle moves relative to the foot and ankle stabilization assembly, there is little to no auxiliary limb movement (i.e., the foot, ankle and leg move as a single segment). The movement in the frontal and transverse plane can accordingly be locked so that cyclic anterior-posterior translations of the tibia/fibula on the femur could be performed at fix loads between 0-150 N to measure AP laxity. With the subject remaining in the same position with thigh and leg stabilized, the sagittal and transverse planes can be locked so that cyclic frontal plane rotations of the tibia/fibula relative to the femur can be measured between 0-10 Nm of varus and valgus rotational torques to measure varus-valgus knee laxity. Finally, with the subject still positioned in the same manner, the frontal plane and sagittal plane can be locked so that transverse plane rotations of the tibia/fibula relative to the femur can occur between 0-5 Nm of internal and external rotation torques to measure internal-external rotation knee laxity. AP translations can be applied via AP loading assembly 600 with anterior-posterior directed loads of the knee relative to U-bar assembly 502 of distal thigh fixation module 650 and thigh cradle 108, in parallel to the joint line, with force measured at the proximal tibia/fibula and displacement measured by sensors that accurately depict relative bone movement between the proximal tibia/fibula and distal femur in the AP plane. In one testing mode, Frontal and Transverse plane knee rotations can be initiated at the base of the leg/foot plate, where IE rotations would occur through the long axis of the tibia/fibula, and frontal plane rotations initiated at the distal tibia/fibula as the base of the leg cradle is moved into varus/valgus along an array of linear slides at 90 degree angles to maintain true VV rotations; in an alternate testing mode, frontal and transverse plant knee rotations can be initiated at the proximal end of the leg cradle though similar mechanisms. Accordingly, in various embodiments, displacement activators can be provided. During conventional, manual testing of the knee joint laxity, clinicians use their hands to provide the force for displacement and the resistance of that force to create "end feel" at the boundaries of the knees range of motion. By contrast, system 700 (see FIG. 18) and a device such as apparatus 100 accomplish displacement using linear tracks that can be actuated either manually or via motors. In at least one embodiment, the motors are controlled by a computer as the computer monitors feedback sensors for force and displacement.

Figure 13:
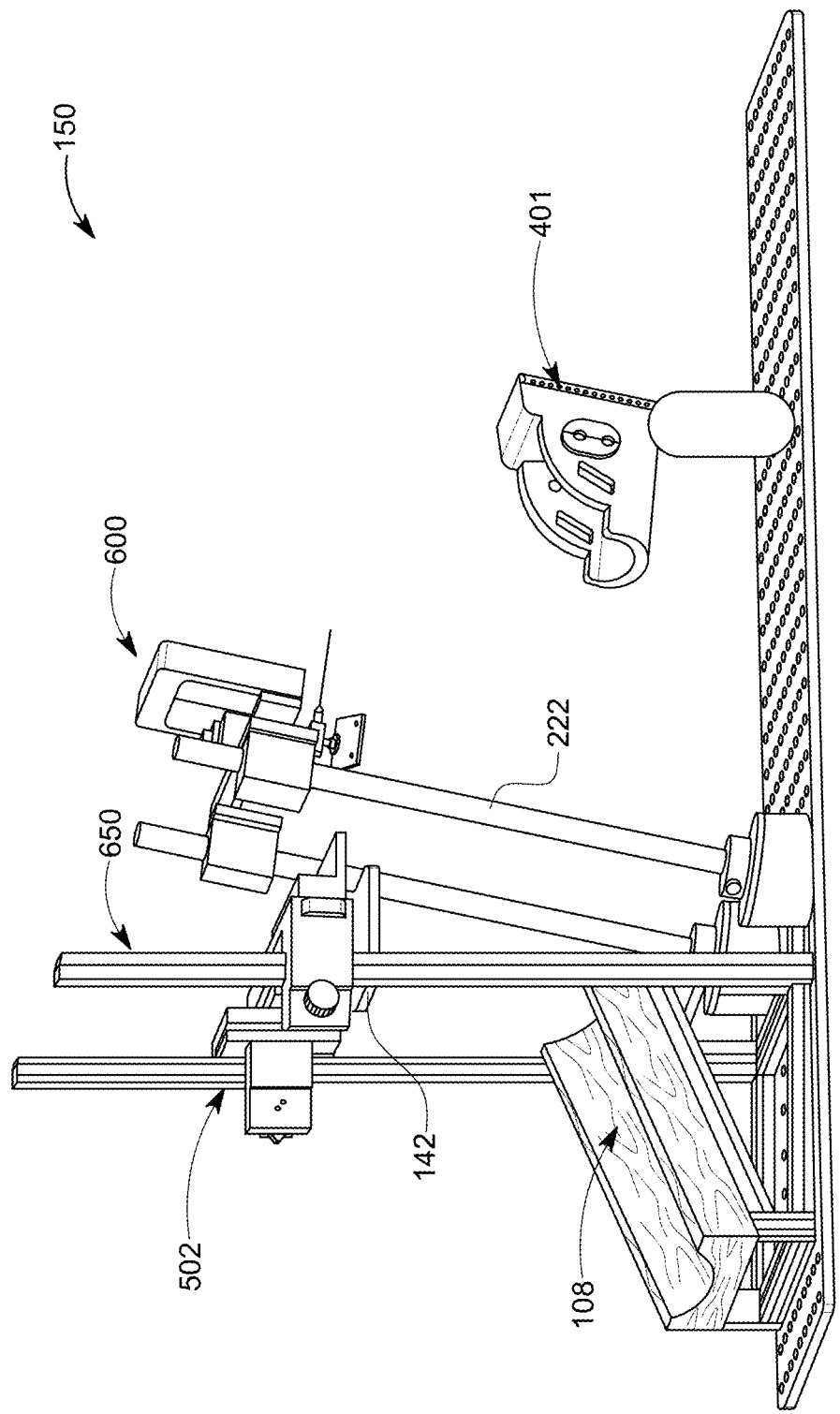
FIG. 13 is a side perspective view of an AP laxity module forming part of a multi-axial joint laxity testing apparatus, according to at least one embodiment.

In some embodiments, apparatus 100 can include various modules such as an AP laxity module 150 (see FIG. 13). AP laxity module 150 can include thigh cradle 108, U-bar assembly 502 that includes a patella pad only (no condylar clamps), AP loading assembly 600 equipped with a load cell and a linear displace sensor, and a heel/foot cradle 401 to position lower limb in neutral or at a predetermined degree (e.g., 15°) of external rotation or internal rotation. In various embodiments, apparatus 100 can further include a module such as a varus-valgus laxity module 250 (see FIG. 14). In various embodiments, varus-valgus laxity module 250 can include thigh clamshell clamps 104, thigh cradle 108, foot and ankle stabilization assembly 400, U-bar assembly 502A that includes a patella pad 142 and a condyle clamp 144. In one embodiment, foot and ankle stabilization assembly 400 is mounted on a curvilinear slide 314 that is fixed to base 102 of the apparatus. In various embodiments, apparatus 100 can also include a module such as an internal-external rotation laxity module 350 (see FIG. 15). In various embodiments, internal-external rotation laxity module 350 can include heel and linear slide 500, foot and ankle stabilization assembly 400, thigh clamshell clamps 104, thigh cradle 108, and U-bar assembly 502A that includes a patella pad 142 and a condyle clamp 144. In at least one embodiment, foot and ankle stabilization assembly 400 is mounted on a heel mechanism with an in-line load cell that is fixed to base of the unit and can be rotated 60 degrees internal rotation and 60 degrees external rotation.

Devices and methods of use thereof as described and enabled herein can be used by physicians (family practice, orthopedic), physician assistants, athletic trainers, physical therapists and other allied health professionals to examine joint integrity to assess injury risk (pre-injury screening), following injury (acute and chronic disease progression), therapeutic results during post-surgical recovery, and rehabilitation. Non-limiting specific applications include: Characterization of laxity profiles in healthy and diseased knees; Monitoring changes in knee laxity with maturation; Screening to identify excessive knee joint laxity in the physically active to identify those at risk for ACL injury; Monitoring disease progression in those with osteoarthritis and other relevant joint diseases; Providing normative data across age (child to older adult) and sex for injury risk screening and satisfactory restoration of function post injury and surgery; Injury Diagnosis; Positioning of joint for radiological examination for stress testing; Objective assessment of injured and un-injured knees to assess ligament integrity (cruciate ligaments and collateral ligaments) and confirm extent of joint instability or "play" following injury without the need for X-ray; Post-Surgical Repair; Confirmation of proper ligament tensioning during surgical reconstruction; Monitoring ligament healing post ligament repair or reconstruction; Training and rehabilitation interventions; Monitoring improvements in joint laxity with therapeutic interventions (e.g., strength training, positive ligament loading); Training tool to induce positive ligament adaptations from applied loads; Monitor ligament healing (primary healing and during rehabilitative process); Custom fitting of knee braces and other knee orthoses designed to protect ligaments and limit knee motion; Excellent tool for research laboratories interested in quantifying the laxity and stiffness profiles of the knee to advance knowledge in all areas noted above; Deploying in the field (e.g., military theatre) to diagnose ligament injury when sophisticated imaging devices are inaccessible; Providing the most comprehensive assessment of joint laxity available on the market (current clinical devices are limited to anterior posterior assessment of joint laxity or rotational laxity).

Table 1 below provides the mean, standard deviation, and range values for clinical measurement of AP, VV and IER Laxity. Descriptive statistics provided in Table 1 include: AKL=anterior knee laxity; PKL=posterior knee laxity; VAR=varus rotational knee laxity; VAL=valgus rotational knee laxity; ER=external rotational knee laxity; IR=internal rotational knee laxity; VARVAL=total varus-valgus rotational knee laxity; and IER=total internal-external rotational knee laxity.

TABLE 1

|  | N | Minimum | Maximum | Mean | Std. Deviation |
| --- | --- | --- | --- | --- | --- |
| AKL_M | 141 | 3.0 | 13.0 | 6.734 | 1.9300 |
| AKL_L | 122 | 3.0 | 13.8 | 7.137 | 2.0072 |
| CAKL_M | 141 | 3.00 | 12.66 | 6.7378 | 1.90621 |
| CAKL_L | 122 | 3.00 | 13.73 | 7.0645 | 2.01787 |
| CPKL_M | 119 | −2.96 | −.88 | −1.7410 | .42378 |
| CPKL_L | 102 | −3.12 | −.84 | −1.7231 | .40086 |
| VAR_M | 141 | −11.8 | −2.1 | −5.337 | 1.6669 |
| VAR_L | 121 | −9.4 | −1.6 | −5.262 | 1.6929 |
| VAL_M | 141 | 2.0 | 13.3 | 6.361 | 1.9948 |
| VAL_L | 121 | 1.9 | 12.5 | 6.101 | 2.2023 |
| ER_M | 141 | 5.8 | 33.0 | 14.729 | 4.9005 |

TABLE 1-continued

|  | N | Minimum | Maximum | Mean | Std. Deviation |
|---|---|---|---|---|---|
| ER_L | 121 | 5.0 | 29.9 | 14.543 | 4.9120 |
| IR_M | 141 | −27.9 | 1.1 | −10.162 | 4.8302 |
| IR_L | 121 | −29.8 | 1.4 | −9.676 | 5.4394 |
| VARVAL_M | 141 | 5.4 | 24.3 | 11.698 | 3.2639 |
| IER_M | 141 | 7.4 | 53.0 | 24.890 | 8.1057 |
| VARVAL_L | 121 | 3.6 | 21.5 | 11.363 | 3.5061 |
| IER_L | 121 | 7.4 | 48.8 | 24.220 | 8.2560 |
| Valid N (listwise) | 98 |  |  |  |  |

Figure 18:
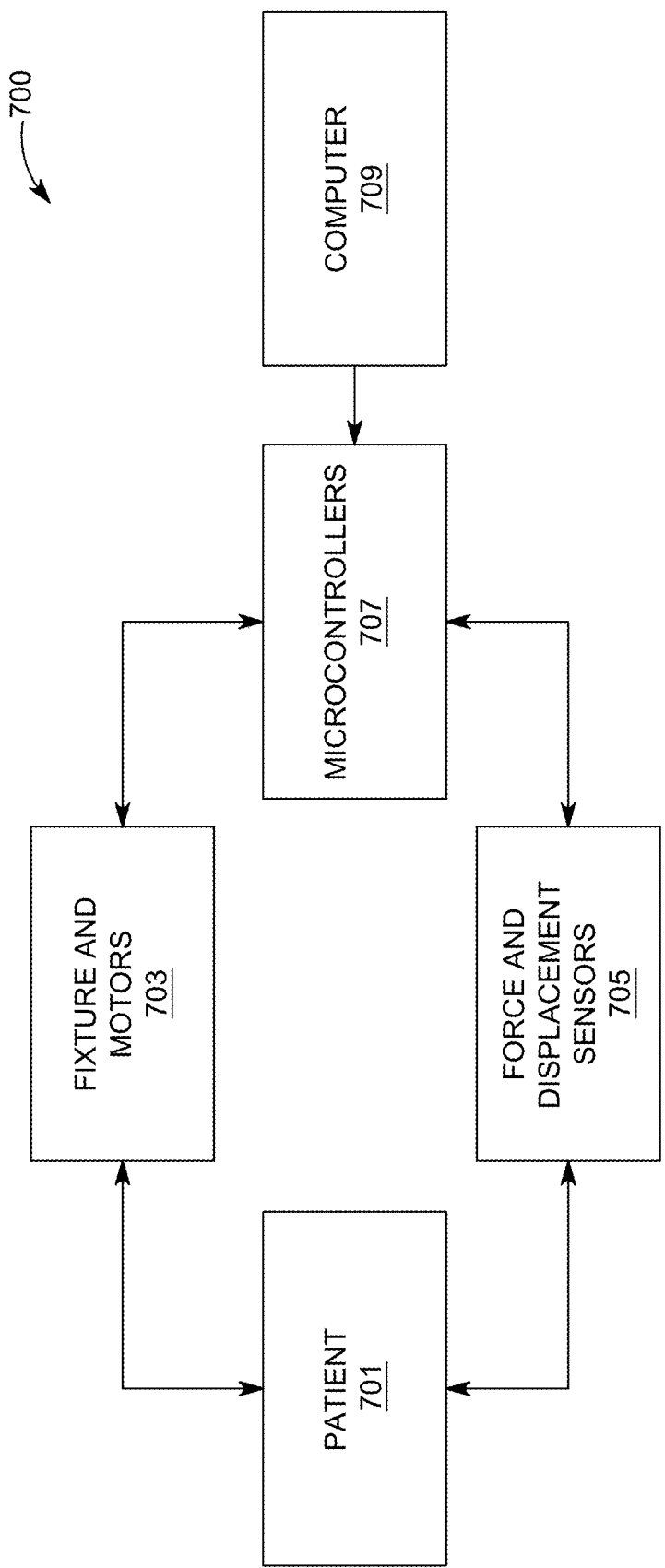
FIG. 18 is a schematic representation of a measurement system for carrying out a multi-axial joint laxity testing using a multi-axial joint laxity testing apparatus, according to at least one embodiment.

In various embodiments, the system including multi-axial joint laxity testing apparatus 100 as disclosed herein can further comprise various components including a patient interface, hardware and software components (see FIG. 18). Accordingly, in various embodiments, the system such as system 700 as illustrated in FIG. 18 can provide for an ergonomic interface between the knee of a patient 701 and the components of apparatus 100 and/or of system 700 such as fixture and motors 703 that apply force to the patient's knee as well as force and displacement sensors 705. Apparatus 100 itself (or the system that includes a device such as apparatus 100) records and analyzes the resulting displacement with one or more microcontrollers 707 in communication with, or forming part of, a computer 709. Computer 709 continuously monitors force and displacement via force and displacement sensors 705 during the test period while controlling the fixture and motors 703 that apply the force required to create displacement. The patient 701 is made to be fully relaxed during the test such that the patient 701 makes no effort to resist the applied force. The product fixture and motors 703 may be directly controlled by the force and displacement sensors 705 as a "fail-safe" in the event of failure of computer 709 that could create harm to patient 701. The apparatus and the system can also be manually driven using the force sensor readouts.

With regard to feedback display, during measurements of laxity, the relationship of mechanical displacement to force applied is determined and displayed on a visual display device coupled to the system or to apparatus 100. Subjectively, this relationship may otherwise be assessed visually and by "feel" that the end user subjectively experiences. The objective measurement made by the system and device as disclosed herein is achieved by essentially curve-fitting discrete recording of force versus displacement as the actuators displace the patient's knee during the test period. These measurements are typically displayed in a simple graph as a hysteretic path as shown, for example, in FIG. 19.

With regard to interface options, the end users that use the system/device is expected to include both technical and non-technical end users. Whereas technical end users may welcome the kind of data presented above, the non-technical user too may appreciate simpler interface such as key numeric test results with the "normal" range of the test. Automatic notices of possible test errors will further ensure high quality results. To appeal to both types of end users, in at least one embodiment, the display will include a "standard" and "advanced" display option that is selectable by the end user.

Disclosed herein is a system 700 for knee joint laxity testing. According to one or more embodiments, the system comprises: a knee joint laxity testing apparatus engaged with a person's knee, the knee joint laxity testing apparatus configured to measure knee laxity values in three planes of motion. A controller is coupled to the knee joint laxity testing apparatus, the controller configured to receive the measured knee laxity values in three planes of motion. An application is configured to display, on a user interface of a computing device, the measured knee laxity values in three planes of motion. According to one or more embodiments, the controller is in communication with at least one motor configured to perform one of: the anterior-posterior translations; the varus-valgus rotations; and the internal-external rotations.

Figure 17:
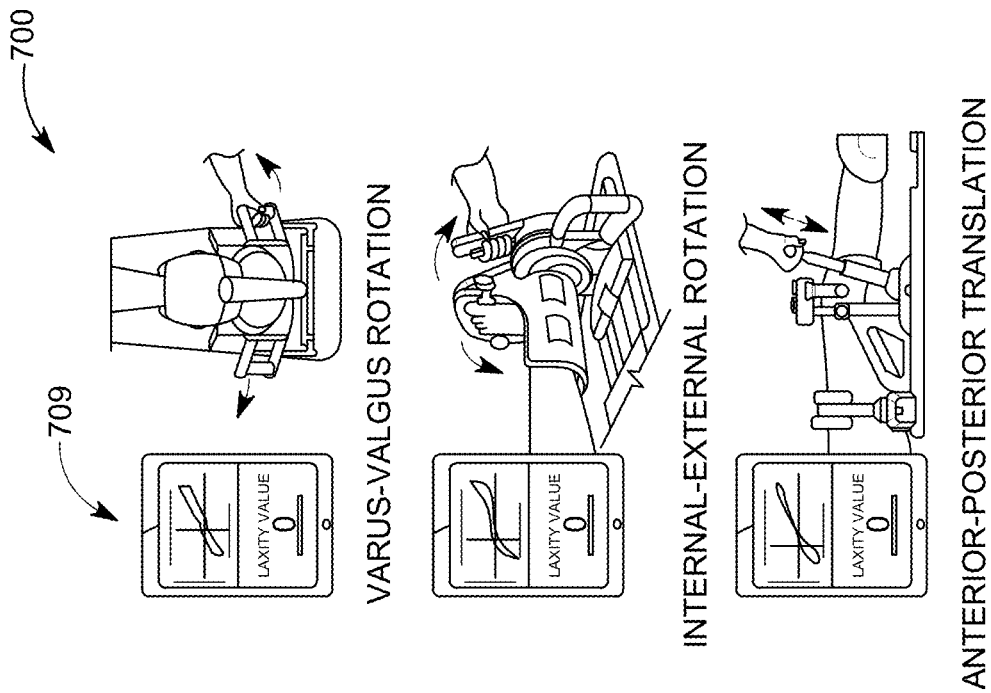
FIG. 17 is a schematic representation of a system for carrying out a multi-axial joint laxity testing using a multi-axial joint laxity testing apparatus, according to at least one embodiment.
Figure 17:
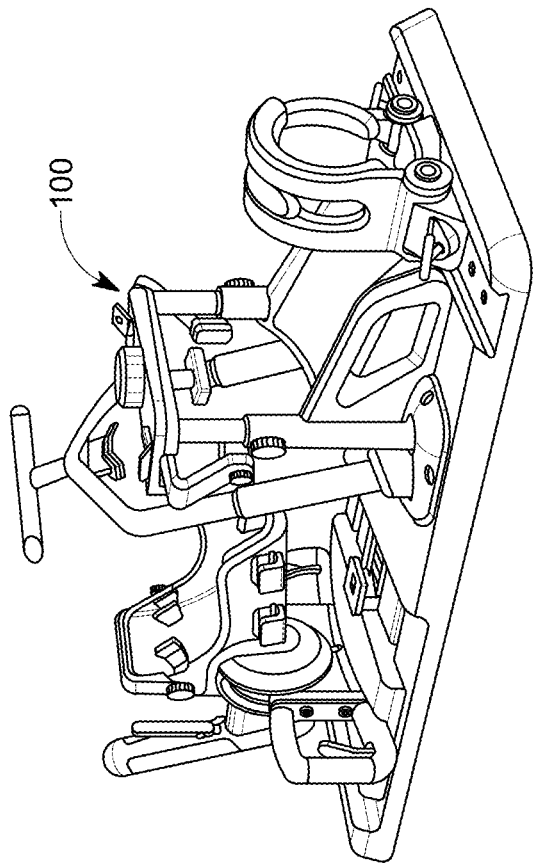

In various embodiments, system 700 can include both a manual and a computer/motor driven version. For the manual version, all loads will be applied manually. With the manual version, the loads and displacements are displayed manually (for e.g., by a simple scale) and also electronically via force and displacements sensors that integrate with the computer to graphically display the force and displacement. System 700 can include three primary variations: (1) fully manual with no peripheral electronics; (2) manual application, with computer interface to display force and displacement (See, for e.g., FIG. 17); and, fully motorized application, where a controller operates the motor to apply the force and receives the data and interface with a computer to display the data.

The tables below describe and define the general requirements of the system/device and are intended to capture end user needs and to guide engineers in the development of technical solutions according to at least one embodiment of the presently disclosed subject matter. The mechanical aspects of the system and device as described herein according to at least one embodiment are provided in Table 2 below.

TABLE 2

| Item | Value | Notes |
|---|---|---|
| Size | 12 in wide × 48 in long × 24 in high | As small a footprint as is possible, e.g., within 28 inches by 72 inches - the dimensions of a typical therapy table. The device may be in daily use and so would not require regular break-down and storage, however, space is typically at a premium in institutions and so smaller is better. The device/system will be reasonably light and portable and can be placed (and removed from a treatment table as needed) and which could also be used in the field. |
| Weight | 25 lbs. or less | The maximum allowable weight for a checked domestic economy bag is typically 50 pounds. While this weight may establish the maximum device weight, a lower weight is desired because the device may likely be moved regularly by the end user or her staff (e.g., on and off an available examination table or to and from storage). |

TABLE 2-continued

| Item | Value | Notes |
| --- | --- | --- |
| Materials | | The non-consumable device components can be chosen to hold up under daily use for a period of at least 5 years' time. Such components include the base, thigh support, knee stabilization parts, sensors and motors.<br>Materials shall be non-toxic and resistant to degradation from common cleaning agents such as bleach, proprietary disinfectants and ultraviolet lamps.<br>Certain mechanical components of the system/device such as, for example, straps and pads may be single use or "consumable". Although the device is not being designed to work within an MRI environment, efforts to avoid or minimize the use of metal is preferred in part for MRI interests but also weight reduction. |

The electrical aspects of the system and device as described herein according to at least one embodiment are provided in Table 3 below.

TABLE 3

| Item | Value | Notes |
| --- | --- | --- |
| Voltage | 120 VAC and 220 VAC | The ability to use 120 VAC and 220 VAC power sources is proposed to help address a wider market (e.g., hospitals, clinics, private practice) |
| Current | Amps | Electrical current will depend upon the specific electromechanical and computer components required to achieve end user needs. |
| Power | Watts | Power will depend upon the voltage and current specifications of the specific electromechanical and computer components, however, sufficient power for startup and "peaks" encountered during use of the product shall be ensured. |

The safety aspects of the system and device as described herein according to at least one embodiment are provided in Table 4 below.

TABLE 4

| Item | Value | Notes |
| --- | --- | --- |
| Electrical Isolation | | The system/device design shall ensure that it does not present an electrical safety issue to the end user, patient or any party that may come into contact with the device (e.g., administrative staff, facilities maintenance personnel).<br>The system/device shall comply with all existing safety standards for medical devices. |
| Force Limitation | ±150N AP force<br>±5 N · m IE torque<br>±10 N · m VV torque | The system/device is configured to be able to generate sufficient force on the patient knee joint to displace the joint for clinical evaluation. Such force, however, needs to be constrained such that no injury is made to the patient's knee by the device.<br>Safety of patients' joint shall be ensured by redundant failure protection such as in the software, at the motor interface and other methods that ensure a tendency for the device to safely "stall" its movement rather than to exceed safe forces and joint displacement.<br>The proposed forces are placeholders only and are based on the values provided in the publication Male-Female Differences in Knee Laxity and Stiffness: A Cadaveric Study, Am J Sports Med. 2015 December; 43(12): 2982-7. [online as of 18 Jul. 2018; https://www.ncbi.nlm.nih.gov/pubmed/264644931. The proposed forces represent the clinical force limits used for testing; thus, actual force limits of the device will be slightly beyond these. |
| General | | General safety design shall be configured to address basic, "common sense" elements, including but not limited to elimination pinch points, sharp edges, abrasive surfaces, and excessive fixture force (i.e., ability to make a mechanical adjustment that could cause injury to the knee joint or cause a measurement error). A patient shut down switch can be |

TABLE 4-continued

| Item | Value | Notes |
|---|---|---|
| | | included in the robotic version. Attention shall be given to how the system/device is affixed to a treatment table such that it cannot shift during use or lead to a patient fall from the therapy table. |

The user interface of the system and device as described herein according to at least one embodiment are provided in Table 5 below.

TABLE 5

| Item | Value | Notes |
|---|---|---|
| Mechanical fixtures and adjustments | | Includes all those mechanical components required to align and secure the patient's leg and knee during laxity measurement by the product. |
| Thigh fixture<br>Patellar fixture<br>Condyle fixtures | Setup in 3 minutes or less<br>N maximum force | Manual adjustments can be reliably made in a quick and effortless fashion, so the end user can focus on the patient and operation of the computer for test.<br>Adjustments shall maintain fixture during the entire duration of the measurement but without cause undue discomfort to the patient or create any injury to the patient. |
| Electromechanical activators | | Includes all those components that are controlled by the computer software during measurement, those sensors that provide feedback to the computer during operation, and those devices that enable the computer control of electromechanical components. |
| Stepper motors<br>Displacement sensors<br>Force sensors | 3 cm maximum linear displacement (A/P)<br>30-degree maximum (V-V) rotational (along an arc that is approximately equal to the average male) displacement and 15 degree maximum (I/E) rotational displacement<br>N maximum force<br>Linear displacement rate<br>Rotational displacement rate | Needs three separate motors, one for each testing motion.<br>At least three load sensors and at least two displacement sensors may be provided in one embodiment.<br>Rate of displacement shall occur within a range that both meets the goals of patient safety and of short test times. |
| Controls | | Controls include all those components required to initiate operation and control the product during measurement, specifically a computer keyboard, mouse, touch-screen and optional remote event marker |
| Computer keyboard, mouse and touch screen<br>Mains power switch<br>Event/remote switch | | Configure to run Windows 10 or higher operating system. Integrated keyboard and mouse, or wireless keyboard and mouse to eliminate wires.<br>One central main power switch is provided that disables all power to the non-computer electrical components (e.g., motors, sensors)<br>Remote key (optional) that annotates an event marker in the data set being collected during test |
| Feedback | | Feedback includes all those components required to provide the end user with guidance on and confirmation of proper product performance |
| Computer display<br>Audio/visual alerts<br>Printed reports | | |

The data analysis, storage, and transmission aspects of the system and device as described herein according to at least one embodiment are provided in Table 6 below.

TABLE 6

| Item | Value | Notes |
|---|---|---|
| System calibration | | Some form of simple two-point calibration to ensure that the force and displacement sensors used for the measurement are working properly and with design tolerances. |
| Sampling rate | | Sample rate that provides sufficient resolution for accurate analysis as provided, for example, in http://mathworld.wolfram.com/NyquistFrequency.html |
| Sensor resolution | | The analog and digital resolution of sensors need to be adequate to ensure accurate analysis. The sensors may have a resolution as indicated in http://www.lionprecision.com/tech-library/technotes/article-0010-sensor-resolution.html |
| Computer hardware and operating system | Intel i5 processor or higher, or other Windows compatible processor (e.g., AMD) | Intel-based with touchscreen and Windows 10. Configuration is intended to help ensure that many off-the-shelf computers may be incorporated into the product solution rather than to require a proprietary computer platform |
| Local storage | 16 Mb RAM 500 Gb HDD or SSD | RAM storage installed in the computer to run software and hold data being collected and analyzed (default is 16 Mb) Hard drive or other storage on the computer that maintains patient data (default is 500 Gb) |

As disclosed herein, a system for knee joint laxity testing comprises: a knee joint laxity testing apparatus engageable with a person's knee, the knee joint laxity testing apparatus comprising a thigh stabilization assembly, a foot and ankle stabilization assembly, and an AP loading assembly, the knee joint laxity testing apparatus configured to measure knee laxity values in three planes of motion. A controller is coupled to the knee joint laxity testing apparatus, the controller configured to receive the measured knee laxity values in three planes of motion. An application is configured to display, on a user interface of a computing device such as computer 709, the measured knee laxity values in three planes of motion.

According to at least one embodiment, the computer 709 (i.e., the computing device) comprises a processor communicably coupled to at least one memory; and program instructions which when executed by the processor cause the processor to: receive, from the controller, the measured knee laxity values in three planes of motion; and, display, on the user interface of the computing device, a level of deviation of a measured knee laxity value from a predetermined value. The controller such as microcontroller 707 is in communication with at least one motor configured to perform one of: the anterior-posterior translations; the varus-valgus rotations; and the internal-external rotations.

According to one or more embodiments, microcontroller 707 is in communication with at least one sensor such as force and displacement sensor 705 configured to sense one or more of a force and a displacement resulting from one of: the anterior-posterior translations; the varus-valgus rotations; and the internal-external rotations.

According to one or more embodiments, the system further comprises receiving, from the controller, the measured knee laxity values in three planes of motion; and, displaying, on the user interface of a computing device, a level of deviation of a measured knee laxity value from a predetermined value.

According to one or more embodiments, the controller such as microcontroller 707 communicates with at least one motor performing one of: the anterior-posterior translations; the varus-valgus rotations; and the internal-external rotations. According to one or more embodiments, microcontroller 707 communicates with at least one sensor configured to sense one or more of a force and a displacement resulting one of: the anterior-posterior translations; the varus-valgus rotations; and the internal-external rotations.

As disclosed herein, a method for measuring knee laxity with a knee joint laxity testing apparatus comprises: measuring knee laxity values in three planes of motion with a knee joint laxity testing apparatus engageable with a person's knee, wherein the knee joint laxity testing apparatus comprises a thigh stabilization assembly, a AP loading assembly, and a foot and ankle stabilization assembly, receiving at a controller coupled to the knee joint laxity testing apparatus the measured knee laxity values; and, displaying, on a user interface of a computing device, the measured knee laxity values.

In some embodiments, the U-bar assembly comprises a U-bar adjustably mounted upon vertical height adjustment bars incorporated into the distal end of the thigh cradle. In some embodiments, the patella pad has a cushioned, deformable, and/or resilient surface which interfaces with the patella region of the knee of a patient to increase comfort and conformity to varying patellar shapes. In some embodiments, the heel cradle is mounted on the IE rotational fixture via a rotary shaft. In some embodiments, the distal thigh fixation module 650 comprises two condyle pads attached to and guided by a respective condyle pad adjustment arm. In some embodiments, the IE rotational fixture is mounted on the carriage via a linear track to facilitate varus-vargus laxity testing. In some embodiments, the distal thigh fixation module further comprises a patella pad mounted to a linear track on an underside of the U-bar assembly. In some embodiments, the condyle pads extend from, and are adjustable relative to, the U-bar assembly. In some embodiments, the method may further include receiving, from the controller, the measured knee laxity values in three planes of motion; and, displaying, on the user interface of a computing device, a level of deviation of a measured knee laxity value from a predetermined value.

Various components of a system according to the exemplary embodiments such as system 700 may be embodied in a program command form which may be executed through various computer units and recorded in computer-readable media. The computer-readable media may contain program commands, data files, data structures, and combinations thereof. The program commands recorded in the medium may be specially designed for the exemplary embodiments. Alternatively, the program commands may be well-known by those skilled in computer software. The computer-readable media may include hardware devices specially configured to store and execute program commands For example, magnetic media, such as a hard disk, a floppy disk and a magnetic tape, optical media, such as a CD-ROM and a DVD, a magneto-optical media, such as a floptical disk, a ROM, a RAM and a flash memory may be used as the computer-readable media. The program commands may include a machine language prepared by a compiler and a high-level language code prepared by an interpreter so as to be executed by a computer. The above-mentioned hardware devices may be configured to operate as one or more software modules to operate the exemplary embodiments and vice versa. As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider). These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Particular embodiments and features have been described with reference to the drawings. It is to be understood that these descriptions are not limited to any single embodiment or any particular set of features, and that similar embodiments and features may arise, or modifications and additions may be made without departing from the scope of these descriptions and the spirit of the appended claims.

As to the above, they are merely specific embodiments of the present invention; however, the scope of protection of the present invention is not limited thereto, and within the disclosed technical scope of the present invention, any modifications or substitutions that a person skilled in the art could readily conceive of should fall within the scope of protection of the present invention. Thus, the scope of protection of the present invention shall be determined by the scope of protection of the appended claims.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

These and other changes can be made to the disclosure in light of the Detailed Description. While the above description describes certain embodiments of the disclosure, and may describe the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

What is claimed is:

1. A knee joint laxity testing apparatus comprising:
   a foot and ankle stabilization assembly disposed on a base for securing a foot and an ankle of a first leg of a person,
     wherein the foot and ankle stabilization assembly comprises
       a foot plate having a foot surface configured to contact the foot of the first leg,
       a heel clamp disposed adjacent the foot surface, and
       a tibial clamp,
     wherein the heel clamp comprises a first member and a second member,
     wherein the tibial clamp comprises a third member and a fourth member,
   wherein the first member is operable to engage a medial side of the first leg,
   wherein the second member is operable to engage a lateral side of the first leg,
   wherein the third member is operable to engage the medial side of the first leg,
   wherein the fourth member is operable to engage the lateral side of the first leg,
     wherein the first member is separately and independently movable, relative to the second member, along an x-axis and along a y-axis along the frontal plane of the first leg,
     wherein movement along the x-axis is in one of a medial direction and a lateral direction and movement along the y-axis is in one of a superior direction and an inferior direction,
     wherein the second member is separately and independently movable, relative to the first member, along the x-axis and the y-axis,
     wherein the third member is separately and independently movable relative to the fourth member, along the x-axis and the y-axis, and
     wherein the fourth member is separately and independently movable, relative to the third member, along the x-axis and the y-axis;
   an anterior-posterior (AP) loading assembly configured to apply an anterior/posterior loading on a knee of the first leg, wherein the anterior-posterior (AP) loading assembly comprises
     a handle in line with a tibial plate,
     wherein the handle and the tibial plate are secured to a central portion of a horizontal bar between two opposed ends,
     wherein the handle is configured to receive a manually applied pushing force from a user against a surface on an opposed side of the handle from the horizontal bar and the manually applied pushing force is configured to be translated to the knee of the first leg through the tibial plate, and
     wherein a portion of the horizontal bar adjacent each end slidably engages one of two parallel guide rails that are mounted to and are angularly adjustable about the x-axis relative to the base and the foot and ankle stabilization assembly,
     wherein the two parallel guide rails together are configured to standardize the direction of the manually applied pushing force translated to the knee of the first leg; and
   a thigh stabilization assembly disposed on the base,
     wherein the thigh stabilization assembly comprises
       a proximal thigh fixation module and a distal thigh fixation module,
     wherein the proximal thigh fixation module comprises
       a thigh cradle and
       a pair of clamshell clamps for securing a thigh of the first leg and disposed on an opposed side of the thigh cradle along the y-axis from the anterior posterior (AP) loading assembly,
     wherein the thigh cradle has a surface including a depression configured to mirror a natural curvature of a posterior portion of the thigh,
     wherein each clamshell clamp comprises a clamshell base and clamping arm and each clamping arm comprise a channel to accept a portion of the clamshell base and aligned apertures configured to accept a lock pin extending through the apertures in the clamping arm and through an opening in the clamshell base such that the clamping arms are pivotable in a medial-lateral direction around the lock pin extending through the opening in the clamshell base and wherein each clamshell clamp has a contoured curvature to enclose a portion of a circumference of the thigh,
wherein the distal thigh fixation module comprises
a U-bar assembly and a patella pad mounted to a horizontal portion of the U-bar assembly operable to firmly hold a distal portion of the thigh of the first leg in place while the first leg is manipulated;
wherein the apparatus is configured to measure knee laxity in three planes of motion.

2. The apparatus of claim 1, wherein the three planes of motion comprise anterior-posterior translations; varus-valgus rotations; and internal-external rotations.

3. The apparatus of claim 1, wherein a spacing between each clamshell base of the pair of the clamshell clamps is slidably adjustable along the x-axis and slidable adjustment is operably controlled by manipulation of an arm knob.

4. The apparatus of claim 1, wherein the foot and ankle stabilization assembly is configured to contact a lower portion of the tibia adjacent the ankle of the first leg, and a heel and a forefoot of the foot of the first leg of the person.

5. The apparatus of claim 1, wherein a first distance defined as a distance between the first member and the second member is adjustable, wherein a second distance defined as a distance between the third member and fourth member is adjustable and wherein the first distance and the second distance are each adjustable independent of the other.

6. The apparatus of claim 1, wherein the anterior-posterior (AP) loading assembly provides anterior/posterior loading solely in a sagittal plane.

7. The apparatus of claim 1, wherein the anterior-posterior (AP) loading assembly further comprises a strap configured to engage a tibial portion of the first leg of the person adjacent a distal side of the knee of the first leg.

8. The apparatus of claim 1, wherein the anterior-posterior (AP) loading assembly further comprises a force transducer in line with the handle and tibial plate.

9. The apparatus of claim 8, wherein the handle includes a position sensor.

10. The apparatus of claim 9, wherein the third member and fourth member of the tibial clamp are each configured to pivot in the medial-lateral and inferior-superior directions, wherein the third member is configured to pivot independently of the fourth member and the heel clamp, and wherein the fourth member is configured to pivot independently of the third member and the heel clamp.

11. The apparatus of claim 1, wherein the distal thigh fixation module is positioned between the anterior-posterior (AP) loading assembly and the thigh cradle.

12. The apparatus of claim 1, wherein the distal thigh fixation module further comprises two condylar clamps affixed to the horizontal portion and the U-bar assembly is attached to the thigh cradle, and wherein the U-bar assembly comprises vertical bars between which the horizontal portion is disposed and to which one of a first end and a second end of the horizontal portion in the x-axis are each engaged and wherein the first end is pivotable about the second end in a medial-lateral direction to facilitate removal of a leg of the person from the apparatus.

13. The apparatus of claim 1, wherein the foot and ankle stabilization assembly further comprises an Internal-External (IE) rotational fixture mounted on a carriage.

14. The apparatus of claim 13, wherein the carriage is attached to a linear track extending along the x-axis or a curvilinear track at least partially extending along the x-axis to facilitate varus-valgus laxity testing.

15. The apparatus of claim 1, wherein the foot and ankle stabilization assembly further comprises rotational mechanisms to allow for Internal-External (IE) rotation and varus-valgus (VV) rotation.

16. A system for knee joint laxity testing, the system comprising:
a knee joint laxity testing apparatus configured to be engageable with a knee of a first leg of a person and measure knee laxity values in three planes of motion, wherein the knee joint laxity testing apparatus comprises a thigh stabilization assembly,
a foot and ankle stabilization assembly, and
an anterior-posterior (AP) loading assembly,
wherein the thigh stabilization assembly comprises a proximal thigh fixation module and
a distal thigh fixation module,
wherein the proximal thigh fixation module comprises
a thigh cradle and
a pair of clamping arms for securing a thigh of a first leg of the person and disposed on an opposed side of the thigh cradle from the anterior-posterior (AP) loading assembly,
wherein the thigh cradle has a surface including a depression configured to mirror the natural curvature of a posterior portion of the thigh of the first leg of the person and
wherein each clamping arm has a contoured curvature to enclose a portion of the circumference of the thigh of the first leg and pivotable about a hinge in a medial-lateral direction,
wherein the distal thigh fixation module comprises a U-bar assembly and
a patella pad mounted to a horizontal portion of the U-bar assembly operable to firmly hold a distal portion of the thigh of the first leg in place while the first leg is manipulated;
wherein the foot and ankle stabilization assembly is configured for securing a foot and an ankle of the first leg of the person and comprises
a foot plate,
a heel clamp, and
a tibial clamp configured to engage the first leg adjacent the ankle of the first leg on a proximal side during use,
wherein the heel clamp comprises a first member and a second member,
wherein the first member is operable to engage a medial side of the first leg,
wherein the second member is operable to engage a lateral side of the first leg,
wherein the first member and second member are configured to be positioned on opposing sides of the first leg,
wherein the first member is separately and independently movable, relative to the second member, along an x-axis and along a y-axis along the frontal plane of the first leg,
wherein the second member is separately and independently movable, relative to the first member, along the x-axis and the y-axis;
wherein the anterior-posterior (AP) loading assembly is configured to apply an anterior/posterior loading on the knee of the first leg and comprises a handle in line with a tibial plate,
wherein the handle and the tibial plate are secured to a central portion of a horizontal bar between two opposed ends,
wherein the handle is configured to receive a manually applied pushing force from a user against a surface on an opposed side of the handle from the horizontal bar and the manually applied pushing force is configured to be translated to the knee of the first leg through the tibial plate, and
wherein a portion of the horizontal bar adjacent each end slidably engages one of two parallel guide rails that are mounted to and are angularly adjustable about the x-axis relative to the base and the foot and ankle stabilization assembly,
wherein the two parallel guide rails together are configured to standardize the direction of the manually applied pushing force translated to the knee of the first leg;
a controller coupled to the knee joint laxity testing apparatus, the controller configured to receive the measured knee laxity values in three planes of motion; and
the controller further configured to display, on a user interface of a computing device, the measured knee laxity values in three planes of motion.

17. The system of claim 16, wherein the computing device comprises a processor communicably coupled to at least one memory; and wherein the memory is configured to store program instructions thereon, which when executed by the processor cause the processor to:
receive, from the controller, the measured knee laxity values in three planes of motion; and
display, on the user interface of the computing device, a level of deviation of a measured knee laxity value from a predetermined value.

18. The system of claim 16, wherein the controller is in communication with at least one motor configured to perform one of: anterior-posterior translations; varus-valgus rotations; and internal-external rotations.

19. The system of claim 16, wherein the controller is in communication with at least one sensor configured to sense one or more of a force and a displacement resulting from one of: anterior-posterior translations; varus-valgus rotations; and internal-external rotations.

20. A method for measuring knee laxity values with a knee joint laxity testing apparatus, comprising:
measuring knee laxity values in three planes of motion with a knee joint laxity testing apparatus engageable with a knee of a first leg of a person, wherein the knee joint laxity testing apparatus comprises
a thigh stabilization assembly,
a foot and ankle stabilization assembly, and
an anterior-posterior (AP) loading assembly,
wherein the thigh stabilization assembly comprises
a proximal thigh fixation module and
a distal thigh fixation module,
wherein the proximal thigh fixation module comprises
a thigh cradle and
a pair of rigid clamping arms for securing a thigh of the first leg and disposed on an opposed side of the thigh cradle from the anterior-posterior (AP) loading assembly
wherein the thigh cradle has a surface including a depression configured to mirror the natural curvature of a posterior portion of the thigh of the first leg,
wherein each clamping arm has a first end and second end with a contoured curvature between the first end and the second end to enclose a portion of a circumference of the thigh and the first end pivotable in a medial-lateral direction about an axis comprising a hinge disposed at the second end,
wherein the distal thigh fixation module comprises
a U-bar assembly and
a patella pad mounted to a horizontal portion of the U-bar assembly operable to firmly hold a distal portion of the thigh of the first leg in place while the first leg is manipulated, and
wherein the thigh cradle is disposed between the rigid pair of clamping arms and the distal thigh fixation module;
wherein the foot and ankle stabilization assembly is configured for securing a foot and an ankle of a person and comprises
a foot plate,
a heel clamp, and
a tibial clamp,
wherein the foot plate is operable to contact a foot of the first leg,
wherein the heel clamp is disposed adjacent to the foot plate and is operable to engage a heel of the first leg, and
wherein the tibial clamp comprises a first support member and a second support member,
wherein the first support member is configured to engage a medial side of the first leg,
wherein the second support member is configured to engage a lateral side of the first leg,
wherein the tibial clamp is configured to only partially surround the first leg such that the anterior side of the first leg is exposed in an anterior direction along a transverse plane extending through the first support member, the second support member, and the first leg; and
wherein the anterior-posterior (AP) loading assembly is configured to apply an anterior/posterior loading on the knee of the first leg and comprises
a handle in line with a tibial plate,
wherein the handle and the tibial plate are secured to a central portion of a horizontal bar between two opposed ends,
wherein the handle is configured to receive a manually applied pushing force from a user against a surface on an opposed side of the handle from the horizontal bar and the manually applied pushing force is configured to be translated to the knee of the first leg through the tibial plate, and
wherein a portion of the horizontal bar adjacent each end slidably engages one of two parallel guide rails that are mounted to and are angularly adjustable relative to the base and the foot and ankle stabilization assembly, and
wherein the two parallel guide rails are configured to standardize the direction of the manually applied pushing force translated to the knee of the first leg.

21. The method of claim 20, further comprising: receiving, by a controller coupled to the knee joint laxity testing apparatus, the measured knee laxity values; and, displaying, on a user interface of a computing device, the measured knee laxity values.

* * * * *